(12) United States Patent
Makin et al.

(10) Patent No.: US 8,333,721 B2
(45) Date of Patent: Dec. 18, 2012

(54) TISSUE-RETAINING SYSTEM FOR ULTRASOUND MEDICAL TREATMENT

(76) Inventors: Inder Raj S. Makin, Loveland, OH (US); Robert Dunki-Jacobs, Mason, OH (US); Richard C. Pellegrino, Upton, MA (US); Michael H. Slayton, Tempe, AZ (US)

( * ) Notice: Subject to any disclaimer, the term of this patent is extended or adjusted under 35 U.S.C. 154(b) by 0 days.

(21) Appl. No.: 12/857,872

(22) Filed: Aug. 17, 2010

(65) Prior Publication Data

US 2010/0312151 A1 Dec. 9, 2010

Related U.S. Application Data

(63) Continuation of application No. 10/152,766, filed on May 22, 2002, now Pat. No. 7,806,892.

(60) Provisional application No. 60/294,135, filed on May 29, 2001.

(51) Int. Cl.
*A61N 7/00* (2006.01)

(52) U.S. Cl. ............ 601/2; 601/3; 601/4; 600/424; 600/425; 600/427; 600/437; 600/439; 600/462; 600/463; 600/466; 600/467; 600/471; 600/472; 600/585

(58) Field of Classification Search ........... 600/424, 600/425, 427, 437, 439, 462, 463, 466, 467, 600/471, 472, 585; 601/2–4
See application file for complete search history.

(56) References Cited

U.S. PATENT DOCUMENTS

| | | | | |
|---|---|---|---|---|
| 4,899,757 A * | 2/1990 | Pope et al. | | 600/463 |
| 5,626,607 A * | 5/1997 | Malecki et al. | | 606/205 |
| 5,779,643 A * | 7/1998 | Lum et al. | | 600/462 |
| 6,007,499 A * | 12/1999 | Martin et al. | | 601/3 |
| 6,010,531 A * | 1/2000 | Donlon et al. | | 623/2.1 |
| 6,266,552 B1* | 7/2001 | Slettenmark | | 600/424 |
| 6,371,973 B1* | 4/2002 | Tepper | | 606/205 |
| 6,432,067 B1* | 8/2002 | Martin et al. | | 601/2 |
| 6,562,033 B2* | 5/2003 | Shah et al. | | 606/41 |
| 7,131,948 B2* | 11/2006 | Yock | | 600/466 |
| 7,806,892 B2* | 10/2010 | Makin et al. | | 606/3 |
| 2007/0004984 A1* | 1/2007 | Crum et al. | | 600/471 |

\* cited by examiner

*Primary Examiner* — Tse Chen
*Assistant Examiner* — Baisakhi Roy
(74) *Attorney, Agent, or Firm* — Michael J Lang

(57) ABSTRACT

An ultrasound medical treatment system includes an end effector insertable into a patient. The end effector includes a tissue-retaining device. The tissue-retaining device includes a first tissue-retaining member having an ultrasound medical-treatment transducer and includes a second tissue-retaining member. The first and second tissue-retaining members are operatively connected together to retain patient tissue between the first and second tissue-retaining members and to release patient tissue so retained. In one example, the second tissue-retaining member has an ultrasound reflector. In the same or a different example, the ultrasound medical-treatment transducer is an ultrasound imaging and medical-treatment transducer.

27 Claims, 15 Drawing Sheets

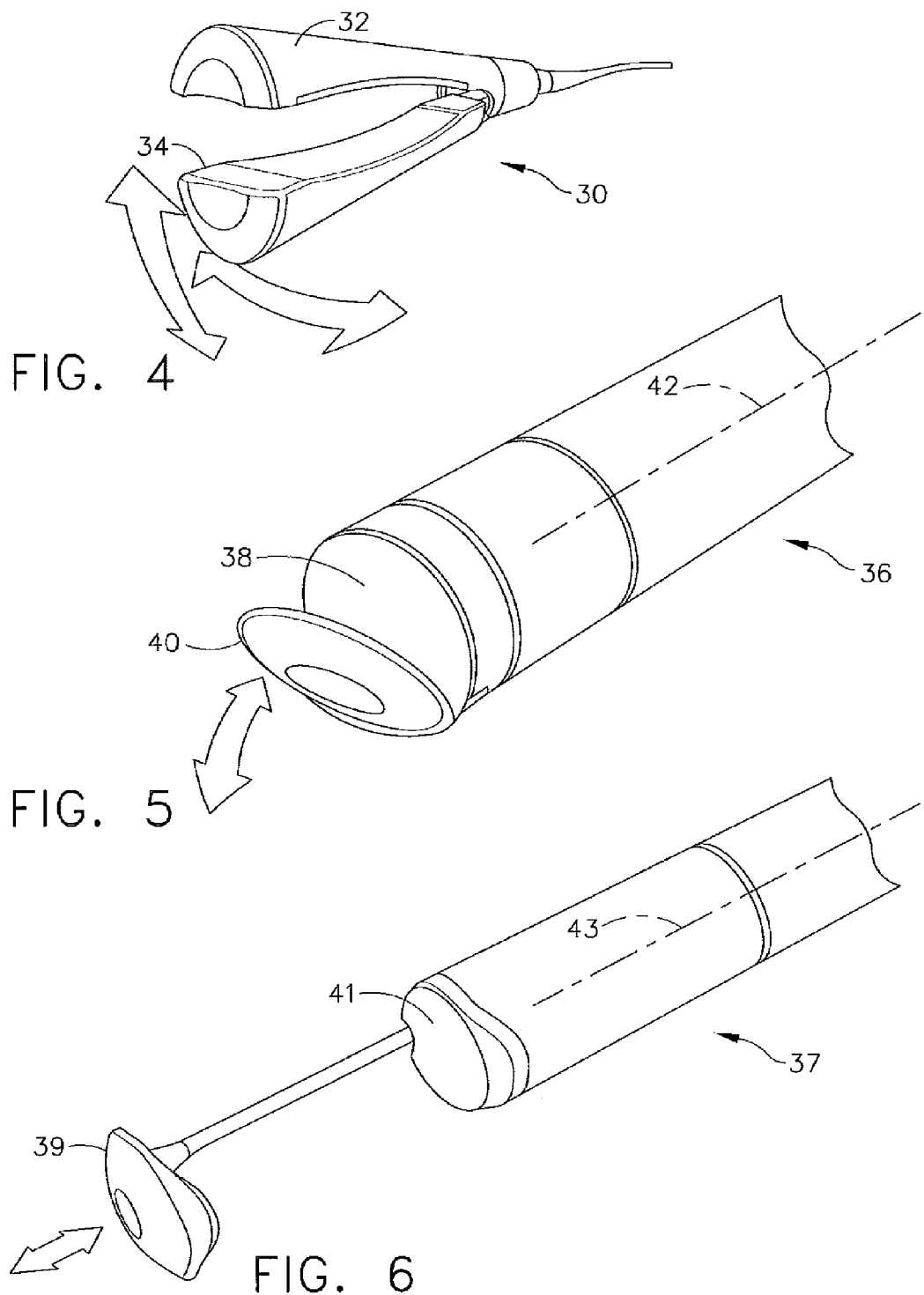

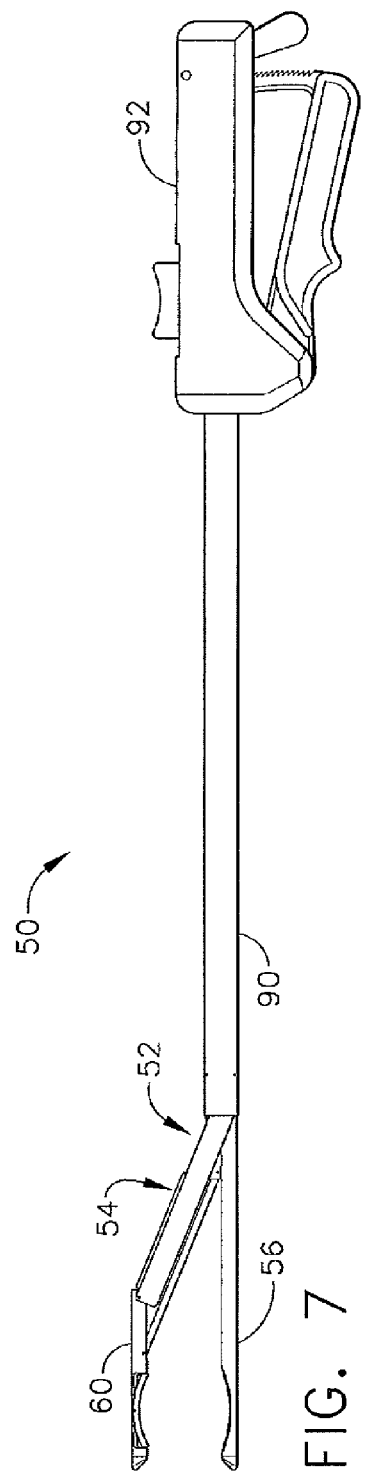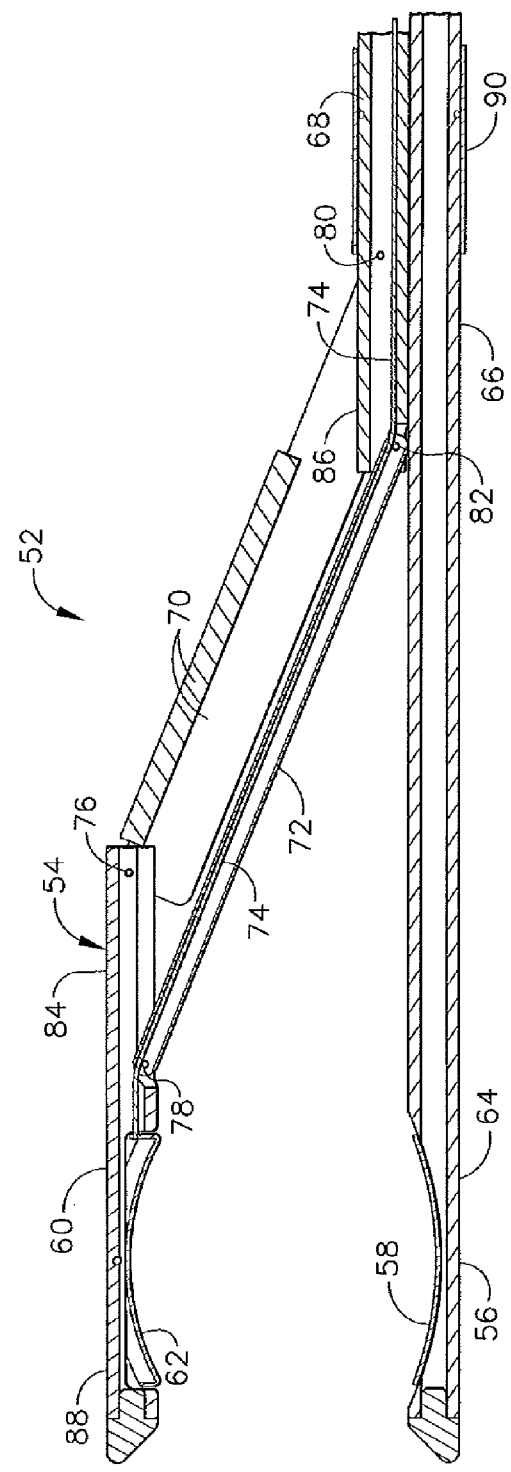

TISSUE-RETAINING SYSTEM FOR ULTRASOUND MEDICAL TREATMENT

REFERENCE TO RELATED APPLICATIONS

The present application is a continuation of U.S. patent application, Ser. No. 10/152,766, filed on May 22, 2002 now U.S. Pat. No. 7,806,892, which claims the priority benefit of U.S. provisional patent application Ser. No. 60/294,135, filed on May 29, 2001, both of which are incorporated herein by reference.

FIELD OF THE INVENTION

The present invention relates generally to ultrasound, and more particularly to an ultrasound medical system and/or to an ultrasound medical method.

BACKGROUND OF THE INVENTION

Known ultrasound medical systems and methods include using ultrasound imaging of patients to identify patient tissue for medical treatment and include using ultrasound to medically destroy identified patient tissue by heating the tissue. Imaging is done at lower power and medical treatment is done at higher power. Low power imaging ultrasound will not medically affect patient tissue. High power medical-treatment ultrasound, when focused at a focal zone a distance away from the ultrasound source, will substantially medically affect patient tissue in the focal zone. However, focused medical-treatment ultrasound will not substantially medically affect patient tissue outside the focal zone such as patient tissue located between the source and the focal zone.

In one known example, a transducer assembly includes a single ultrasound transducer having a single transducer element, or an array of transducer elements acting together, to ultrasonically image the patient and to ultrasonically ablate identified patient tissue. It is known to convert ultrasound imaging data into temperature imaging data for ultrasound-treated patient tissue to monitor the ultrasound treatment. A known transducer element includes a transducer element having a concave shape or an acoustic lens to focus ultrasound energy. A known array of transducer elements includes a planar, concave, or convex array of transducer elements to focus ultrasound energy. A known array of transducer elements includes an array whose transducer elements are electronically or mechanically controlled together to steer and focus the ultrasound emitted by the array to a focal zone (which may be large or which may be as small as, for example, a grain of rice) to provide three-dimensional medical ultrasound treatment of patient tissue. In some applications, the transducer is placed on the surface of patient tissue for ultrasound imaging and/or ultrasound medical treatment of areas within the patient tissue. In other applications, the transducer is surrounded with a balloon which is expanded to contact the surface of patient tissue by filling with a fluid such as a saline solution to provide acoustic coupling between the transducer and the patient tissue.

Known ultrasound medical systems and methods include deploying an end effector having an ultrasound transducer outside the body to break up kidney stones inside the body, endoscopically inserting an end effector having an ultrasound transducer in the colon to medically destroy prostate cancer, laparoscopically inserting an end effector having an ultrasound transducer in the abdominal cavity to medically destroy a cancerous liver tumor, intravenously inserting a catheter end effector having an ultrasound transducer into a vein in the arm and moving the catheter to the heart to medically destroy diseased heart tissue, and interstitially inserting a needle end effector having an ultrasound transducer needle into the tongue to medically destroy tissue to reduce tongue volume to reduce snoring. Known methods for guiding an end effector within a patient include guiding the end effector from x-rays, from MRI images, and from ultrasound images obtained using the ultrasound transducer. Known ultrasound imaging includes Doppler ultrasound imaging to detect blood flow, and a proposed known use of ultrasound includes using an ultrasound transducer outside the body to stop internal bleeding (by sealing ruptured blood vessels) of a patient brought to an emergency room of a hospital.

A Mammotome® Breast Biopsy System manufactured by Ethicon Endo-Surgery, Inc. (a Johnson & Johnson Company) inserts a tube into breast tissue, wherein the tube contains an end effector having a biopsy cutting tool. A known electromagnetic transponder and three-receiver system for calculating the position of the transponder and for guiding the transponder (which is attached to a heart catheter for monitoring the heart) inside a patient is the CARTO™ EP Navigation System used with a NAVI-STAR® catheter manufactured by Biosense Webster (a Johnson & Johnson Company). Further, it is known that changes in patient tissue because of medical treatment of patient tissue, such as ultrasound medical treatment, affect the amplitude and/or phase of ultrasound imaging signals.

What is needed is an improved ultrasound medical system and/or an improved ultrasound medical method. This invention addresses those needs lacking in an ultrasonic medical system and/or an ultrasonic medical method.

SUMMARY OF THE INVENTION

One expression of an embodiment of the invention is an ultrasound medical treatment system including an end effector insertable into a patient. The end effector includes a tissue-retaining device. The tissue-retaining device includes a first tissue-retaining member having an ultrasound medical-treatment transducer and includes a second tissue-retaining member. The first and second tissue-retaining members are operatively connected together to retain patient tissue between the first and second tissue-retaining members and to release patient tissue so retained. In one example, the second tissue-retaining member has an ultrasound reflector. In the same or a different example, the ultrasound medical-treatment transducer is an ultrasound imaging and medical-treatment transducer.

The present invention has, without limitation, application in conventional endoscopic and open surgical instrumentation as well as application in robotic-assisted surgery.

BRIEF DESCRIPTION OF THE DRAWINGS

FIG. 4 is a perspective view of a first alternate end effector which can be used in the ultrasound medical treatment system of FIG. 1;

FIG. 5 is a perspective view of a second alternate end effector which can be used in the ultrasound medical treatment system of FIG. 1;

FIG. 6 is a perspective view of a third alternate end effector which can be used in the ultrasound medical treatment system of FIG. 1;

FIG. 7 is a side elevational view of a second embodiment of the present invention showing another ultrasound medical treatment system which includes a tissue-retaining device;

FIG. 8 is an enlarged, partially-cutaway view of the end effector of the ultrasound medical treatment system of FIG. 7;

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, expressions of embodiments, examples, methods, etc. can be combined with any one or more of the other following-described embodiments, expressions of embodiments, examples, methods, etc. For example, and without limitation, any of the end effectors can be used in any of the methods, any of the transducer arrangements can be used in any of the end effectors, and any appropriate methods can be combined such as combining the seventeenth and twentieth methods, etc.

Ultrasound Medical Treatment Using
Tissue-Retaining Devices

Tissue-Retaining System for Ultrasound Medical Treatment

Figure 1:
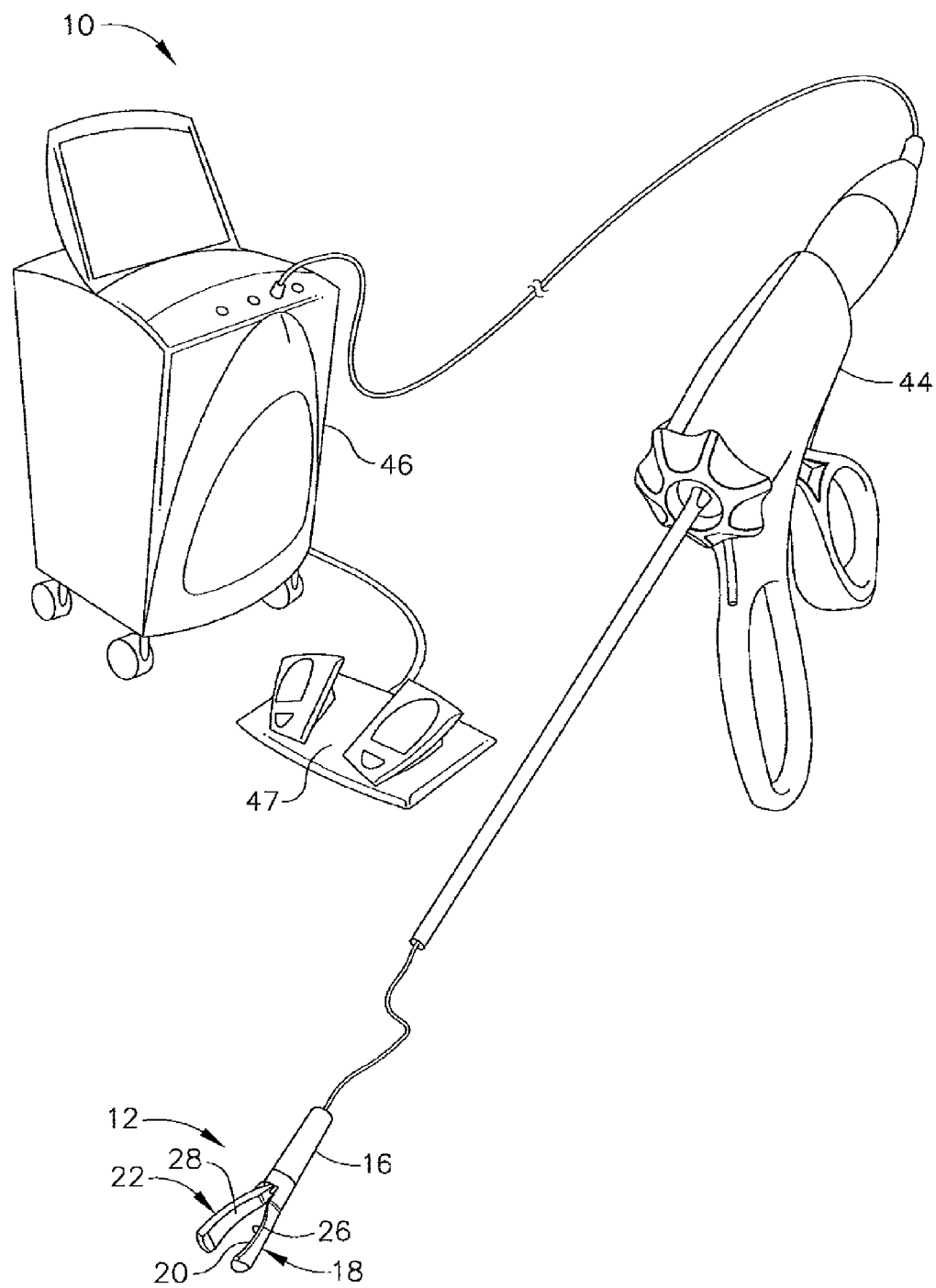
FIG. 1 is a perspective view of a first embodiment of the present invention showing an ultrasound medical treatment system which includes a tissue-retaining device.
Figure 2:
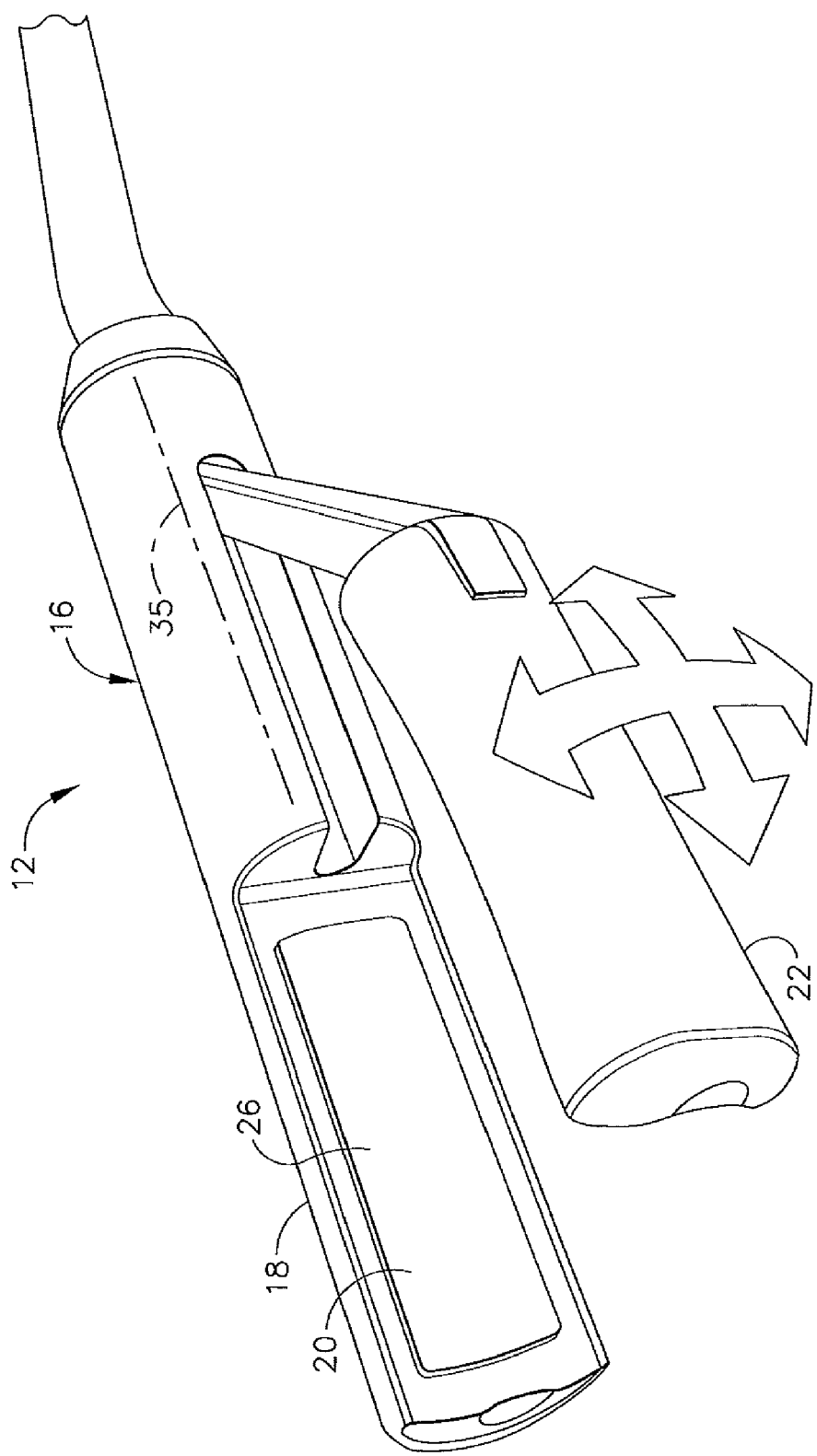
FIG. 2 is an enlarged view of the end effector of the ultrasound medical treatment system of FIG. 1.
Figure 3:
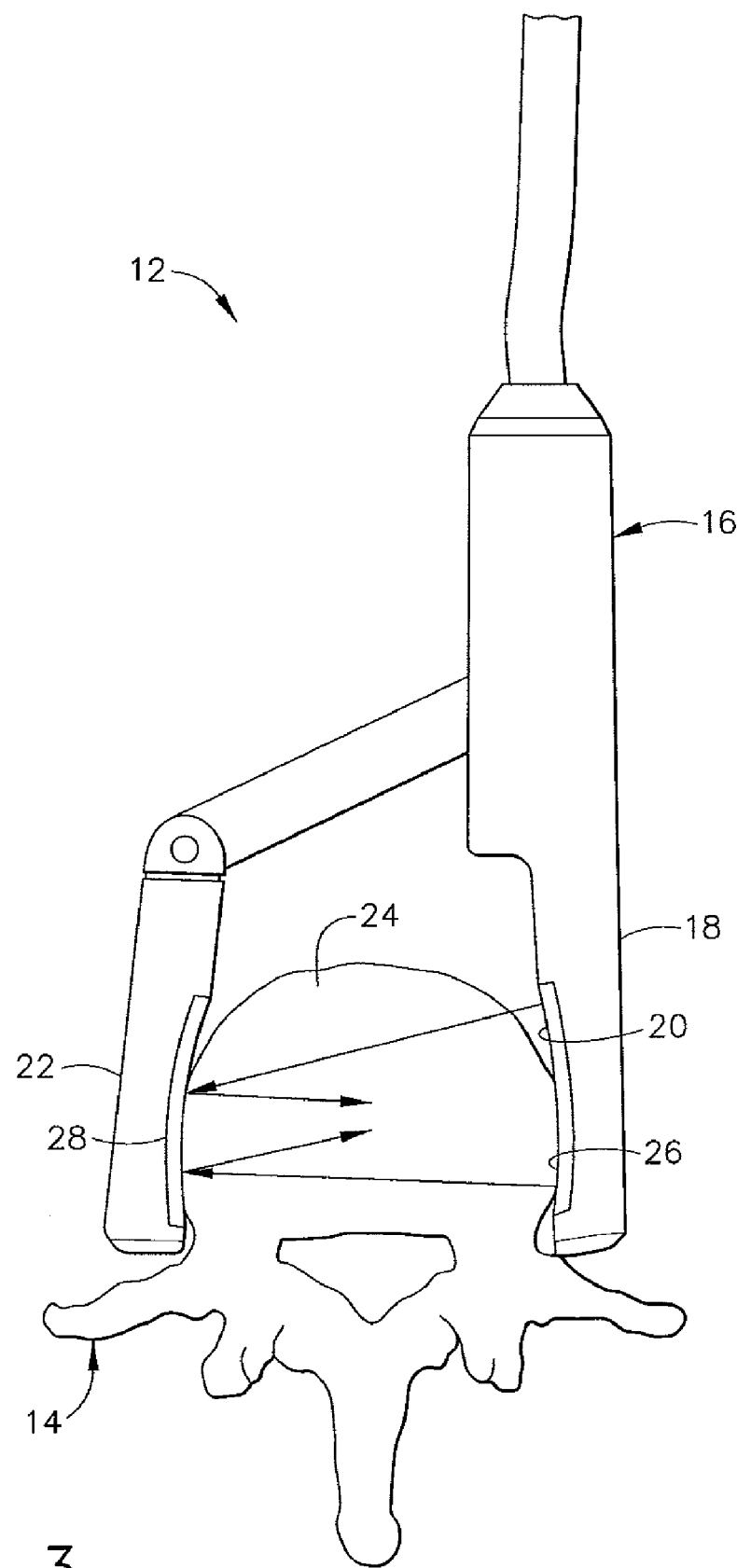
FIG. 3 is a view of the end effector of FIG. 2 retaining an intervertebral disk of a patient.

Referring now to the drawings, FIGS. 1-3 illustrate a first embodiment of the present invention. A first expression of the first embodiment of the present invention is for an ultrasound medical treatment system 10 including an end effector 12 insertable into a patient 14. The end effector 12 includes a tissue-retaining device 16. The tissue-retaining device 16 includes a first tissue-retaining member 18 having an (i.e., at least one) ultrasound medical-treatment transducer 20 (also called "transducer 20") and includes a second tissue-retaining member 22. The first and second tissue-retaining members 18 and 22 are operatively connected together to retain patient tissue 24 between the first and second tissue-retaining members 18 and 22 and to release patient tissue 24 so retained.

It is noted that an ultrasound medical-treatment transducer is an ultrasound transducer adapted at least for ultrasound medical treatment of a patient such as, but not limited to, a human patient. An ultrasound medical-treatment transducer includes either a single ultrasound medical-treatment transducer element or an array of ultrasound medical-treatment transducer elements, as is known to those skilled in the art. An ultrasound medical-treatment transducer may or may not also be adapted for ultrasound imaging of a patient. Likewise, an ultrasound imaging transducer is an ultrasound transducer adapted at least for ultrasound imaging of a patient and may or may not also be adapted for ultrasound medical-treatment of a patient.

Advantages of retaining patient tissue between two tissue-retaining members during ultrasound medical treatment by one of the tissue-retaining members include having a single instrument which ultrasonically medically treats patient tissue and at the same time immobilizes patient tissue against undesired movement during the treatment. It is also noted that in one application the tissue-retaining device is a clamp which retains and holds tissue and that in another application the tissue-retaining device retains tissue against movement, but does not hold tissue, and therefore is not a clamp.

In one variation, not shown, the second tissue-retaining member 22 has an ultrasound imaging and/or medical treatment transducer. In the same or a different variation, not shown, the tissue-retaining device 16 has at least one additional tissue-retaining member. Mechanisms, not shown, for remotely moving two (or more) members toward and away from each other are within the ordinary level of skill of the artisan and include, without limitation, the use of pivotal member attachments and the use of cables or motors. In the same or a different variation, the retained patient tissue 24 is retained between the ultrasound medical-treatment transducer 20 and the second tissue-retaining member 22. In the same or a different variation, the ultrasound medical-treatment transducer 20 focuses ultrasound energy, such focusing being known to those skilled in the art. In the same or a different variation, not shown, the second tissue-retaining member 22 is substantially ultrasonically non-reflective.

A second expression of the first embodiment of the present invention is for an ultrasound medical treatment system 10 including an end effector 12 insertable into a patient 14. The end effector 12 includes a tissue-retaining device 16. The tissue-retaining device 16 includes a first tissue-retaining member 18 having an (i.e., at least one) ultrasound imaging and medical-treatment transducer 26 (also called "transducer 26") and includes a second tissue-retaining member 22. The first and second tissue-retaining members 18 and 22 are operatively connected together to retain patient tissue 24 between the first and second tissue-retaining members 18 and 22 and to release patient tissue 24 so retained.

It is noted that an ultrasound imaging and medical-treatment transducer is an ultrasound transducer adapted at least for both ultrasound imaging and ultrasound medical treatment of a patient. An ultrasound imaging and medical-treatment transducer includes either a single ultrasound imaging and medical-treatment transducer element or an array of ultrasound medical transducer elements (including an array having at least one separate element for imaging and at least one separate element for medical treatment or an array having at least two elements each adapted for both imaging and medical treatment), as is known to those skilled in the art. In one variation, the retained patient tissue 24 is retained between the imaging and medical-treatment transducer 26 and the second tissue-retaining member 22. In the same or a different variation, the ultrasound imaging and medical-treatment transducer 26 focuses ultrasound energy. In the same or a different variation, not shown, the second tissue-retaining member 22 is substantially ultrasonically non-reflective.

A third expression of the first embodiment shown in FIGS. 1-3 is for an ultrasound medical treatment system 10 including an end effector 12 insertable into a patient 14. The end effector 12 includes a tissue-retaining device 16. The tissue-retaining device 16 includes a first tissue-retaining member 18 having an (i.e., at least one) ultrasound medical-treatment transducer 20 and includes a second tissue-retaining member 22 having an (i.e., at least one) ultrasound reflector 28. The first and second tissue-retaining members 18 and 22 are operatively connected together to retain patient tissue 24 between the first and second tissue-retaining members 18 and 22 and to release patient tissue 24 so retained.

Advantages of retaining patient tissue between two tissue-retaining members during ultrasound medical treatment by an ultrasound medical-treatment transducer of a first tissue-retaining member and an ultrasound reflector of a second tissue-retaining member include having a single instrument which ultrasonically medically treats patient tissue by direct ultrasound, which enhances the ultrasound medical treatment by reflected ultrasound, and which at the same time immobilizes patient tissue against undesired movement during the treatment.

It is noted that an ultrasound reflector 28 is a material which reflects ultrasound at least to a degree that would substantially medically affect patient tissue over a treatment period by direct ultrasound which is being reflected back by the ultrasound reflector. Choices of ultrasound reflecting materials include, without limitation, acoustically-rigid materials such as stainless steel (which reflects about 100%) and aluminum (which reflects about 80%) and acoustically-softer materials such as corporene (which reflects about 90%). An ultrasound reflecting material is contrasted with an ultrasound absorbing material such as, without limitation, rubber or plastic. In one variation, the retained patient tissue 24 is retained between the ultrasound medical-treatment transducer 20 and the ultrasound reflector 28. In the same or a different variation, the ultrasound medical-treatment transducer 20 and the ultrasound reflector 28 each focus ultrasound energy, such ultrasound reflector focusing being accomplished by the shape of, or by shaping, the reflector surface as is within the ordinary level of skill of the artisan.

A fourth expression of the first embodiment shown in FIGS. 1-3 is for an ultrasound medical treatment system 10 including an end effector 12 insertable into a patient 14. The end effector 12 includes a tissue-retaining device 16. The tissue-retaining device 16 includes a first tissue-retaining member 18 having an (i.e., at least one) ultrasound imaging and medical-treatment transducer 26 and includes a second tissue-retaining member 22 having an (i.e., at least one) ultrasound reflector 28. The first and second tissue-retaining members 18 and 22 are operatively connected together to retain patient tissue 24 between the first and second tissue-retaining members 18 and 22 and to release patient tissue 24 so retained. In one variation, the retained patient tissue 24 is retained between the ultrasound imaging and medical-treatment transducer 26 and the ultrasound reflector 28. In the same or a different variation, the ultrasound imaging and medical-treatment transducer 26 and the ultrasound reflector 28 each focus ultrasound energy.

In one example of the previously-described third and fourth expressions of the first embodiment, the ultrasound reflector 28 is disposed to receive ultrasound energy from the transducer 20 and 26 and is oriented to reflect the received ultrasound energy back into patient tissue 24 retained by the tissue-retaining device 16. In the same or a different example, the ultrasound reflector 28 is oriented to reflect the received ultrasound energy away from the transducer 20 and 26 when the patient tissue 14 is retained by the tissue-retaining device 16. An advantage of this arrangement is that it avoids damage to the transducer from the reflected ultrasound. In the same or a different example, one of the first and second tissue-retaining members 18 and 22 is controllably orientatable relative to the other of the first and second tissue-retaining members 18 and 22 such as, without limitation, by being orientatable along the double-headed arrows shown in FIG. 2. In one modification, the second tissue-retaining member 22 is controllably orientatable relative to the first tissue-retaining member 18 to reflect the received ultrasound energy back along different directions. A first alternate end effector 30 is shown in FIG. 4 wherein the second tissue-retaining member 32 is controllably orientatable relative to the first tissue-retaining member 34 as shown by the double-headed arrows in FIG. 4. Mechanisms, not shown, for remotely controlling the orientation of one member relative to another member are within the ordinary level of skill of the artisan and include, without limitation, the use of pivotal member attachments and the use of cables or motors. In one application, the transducer 20 and 26 generates wide-focused ultrasound (shown by the two single-headed arrows coming from the first tissue-retaining member 18 in FIG. 3) and the ultrasound reflector 28 generates narrow-focused ultrasound (shown by the two single-headed arrows coming from the second tissue-retaining member 22 in FIG. 3).

In one example of the previously-described first through fourth expressions of the first embodiment, the end effector 12 is an open-surgery end effector, an endoscopic end effector, a laparoscopic end effector (as shown in FIG. 1), a catheter end effector (such as, but not limited to, an intravascular catheter end effector), or a needle end effector, as can be appreciated by those skilled in the art. In one application, the end effector 12 is used to retain a blood vessel and then to ultrasonically treat the blood vessel to seal the blood vessel stopping the flow of blood in the retained blood vessel. In another application, the end effector 12 is used to retain patient tissue and then to ultrasonically ablate at least a portion of the retained patient tissue.

In one design of the previously-described first through fourth expressions of the first embodiment, the end effector 12 has a longitudinal axis 35, and one of the first and second tissue-retaining members 18 and 22 at all times faces along a direction which is substantially perpendicular to the longitudinal axis 35. If the one tissue-retaining member were planar, this means that the longitudinal axis would be substantially parallel to the plane of the one tissue-retaining member. In one enablement, the one tissue-retaining member is the first tissue-retaining member 18. A second alternate end effector 36 has first and second tissue-retaining members 38 and 40 which are hinged together to relatively move as indicated by the double-headed arrow and which are shown in a partially open configuration in FIG. 5. The second alternate end effector 36 has a longitudinal axis 42, and one of the first and second tissue-retaining members 38 and 40 at all times faces along a direction which is substantially parallel to the longitudinal axis 42. If the one tissue-retaining member were planar, this means that the longitudinal axis would be substantially perpendicular to the plane of the one tissue-retaining member. In one enablement, the one tissue-retaining member is the first tissue-retaining member 38. A third alternate end effector 37 having first and second tissue-retaining members 39 and 41 with one member longitudinally movable with respect to the other member (as indicated by the double-headed arrow) is shown in FIG. 6. The third alternate end effector 37 has a longitudinal axis 43, and one of the first and second tissue-retaining members 39 and 41 at all times faces along a direction which is substantially parallel to the longitudinal axis 43. In one enablement, the one tissue-retaining member is the first tissue-retaining member 39.

In one enablement, as shown in FIG. 1, the ultrasound medical treatment system 10 also includes a handpiece 44 operatively connected to the end effector 12 and to an ultrasound controller 46 operatively connected to a foot-pedal power switch 47, as can be appreciated by those skilled in the art.

A first method of the invention is for ultrasound medical treatment of a patient and uses the ultrasound medical treatment system as previously described in the first, second, third or fourth expression of the first embodiment with or without the previously-described variations, etc. thereof. The first method includes steps a) through e). Step a) includes endoscopically inserting the end effector into an ear, nose, or throat of the patient. Step b) includes guiding the end effector in the patient. Step c) includes identifying patient tissue for medical treatment such as optionally at least in part from ultrasound imaging using the transducer. Other ways of identifying patient tissue for medical treatment include, without limitation, using x-rays and/or MRI imaging, as are known to the artisan. Step d) includes retaining the identified patient tissue using the tissue-retaining device. Step e) includes medically treating the retained patient tissue with ultrasound using the transducer or using the transducer and the ultrasound reflector. In one implementation, one tissue-retaining member at all times faces along a direction which is substantially parallel to the longitudinal axis of the end effector (as seen in FIGS. 5 and 6).

A second method of the invention is for ultrasound medical treatment of a patient and uses the ultrasound medical treatment system as previously described in the first, second, third or fourth expression of the first embodiment with or without the previously-described variations, etc. thereof. The second method includes steps a) through c). Step a) includes inserting the end effector 12 into the patient. Step b) includes retaining an intervertebral disk 48 (see FIG. 3) of the patient with the tissue-retaining device, wherein the intervertebral disk 48 includes tissue. Step c) includes medically treating the retained intervertebral disk 48 with ultrasound to shrink the tissue using the transducer or using the transducer and the ultrasound reflector. In one implementation, one tissue-retaining member at all times faces along a direction which is substantially perpendicular to the longitudinal axis of the end effector (as seen in FIGS. 2 and 4). In one application of the second method of the invention, the intervertebral disk 48 includes connective and nerve tissue.

A third method of the invention is for ultrasound medical treatment of a patient and uses the ultrasound medical treatment system as previously described in the first, second, third or fourth expression of the first embodiment with or without the previously-described variations, etc. thereof. The third method includes steps a) through c). Step a) includes inserting the end effector into the patient. Step b) includes retaining a joint of the patient with the tissue-retaining device, wherein the joint includes tissue. Step c) includes medically treating the retained joint with ultrasound to shrink the tissue using the transducer or using the transducer and the ultrasound reflector. In one implementation, one tissue-retaining member at all times faces along a direction which is substantially perpendicular to the longitudinal axis of the end effector (as seen in FIGS. 2 and 4). In one application of the third method of the invention, the joint includes connective and nerve tissue.

As previously mentioned, one application of the ultrasound medical treatment system 10 of the previously-described first through fourth expressions of the first embodiment uses the tissue-retaining device to retain a blood vessel and uses the transducer, or the transducer and the ultrasound reflector, to substantially stop the flow of blood within the blood vessel.

Referring again to the drawings, FIGS. 7-8 illustrate a second embodiment of the present invention which is an ultrasound medical treatment system 50 including an end effector 52 insertable into a patient. The end effector 52 includes a tissue-retaining device 54. The tissue-retaining device 54 includes a first tissue-retaining member 56 having an ultrasound imaging and medical-treatment transducer 58 and includes a second tissue-retaining member 60 having an ultrasound reflector 62. The first and second tissue-retaining members 56 and 60 are operatively connected together to retain patient tissue between the first and second tissue-restraining members and to release patient tissue so retained.

The first and second tissue-retaining members 56 and 60 always maintain a substantially parallel alignment.

Advantages of having a substantially parallel alignment between the tissue-retaining members include, in one example, having the transducer and the ultrasound reflector maintain a substantially parallel alignment for improved reflected ultrasound medical treatment enhancement for any thickness of patient tissue retained by the tissue-retaining members.

In one example of the second embodiment, the first tissue-retaining member 56 is a distal end portion 64 of a first tube 66. The ultrasound medical treatment system 50 also includes a second tube 68, first and second link members 70 and 72, and a cable 74. The second tube 68 is oriented substantially parallel to the first tube 66. The first and second link members 70 and 72 are pivotally attached to the second tissue-retaining member 60 and to the second tube 68 at pivot points 76-82 creating a hinged parallelogram defined by a proximal portion 84 of the second tissue-retaining member 60, a distal portion 86 of the second tube 68, and the first and second link members 70 and 72. The ultrasound reflector 62 is disposed at a distal portion 88 of the second tissue-retaining member 60 and faces the transducer 58. The cable 74 is operatively connected to the hinged parallelogram to move the second tissue-retaining member 60 toward and away from the first tissue-retaining member 56.

In one variation, the ultrasound medical treatment system 50 also includes an outer tube 90. The cable 74 and the first and second tubes 66 and 68 are disposed in the outer tube 90. In one modification, the ultrasound medical treatment system 50 also includes a handpiece 92. The cable 74 and the first, second, and outer tubes 66, 68 and 90 are operatively connected to the handpiece 92. In one design, the orientation of the first tube 66 about the longitudinal axis of the first tube 66 is controlled by a step motor (not shown) disposed in, and actuated by, the handpiece 92. In the same or another design, the first tube 66 is a hollow tube allowing for transducer wiring (not shown), and the second tube is a solid tube (not shown). Depending on use, the tubes 66, 68, and 90 may be rigid or flexible which also is true for any tube arrangement (specifically disclosed as rigid or flexible, or not so specifically disclosed) of any end effector and for any end effector itself of any of the previous or following embodiments of the invention.

Ultrasound Medical Treatment Using Specific Transducer Arrangements

Deployable Ultrasound Medical Transducers

Figure 9:
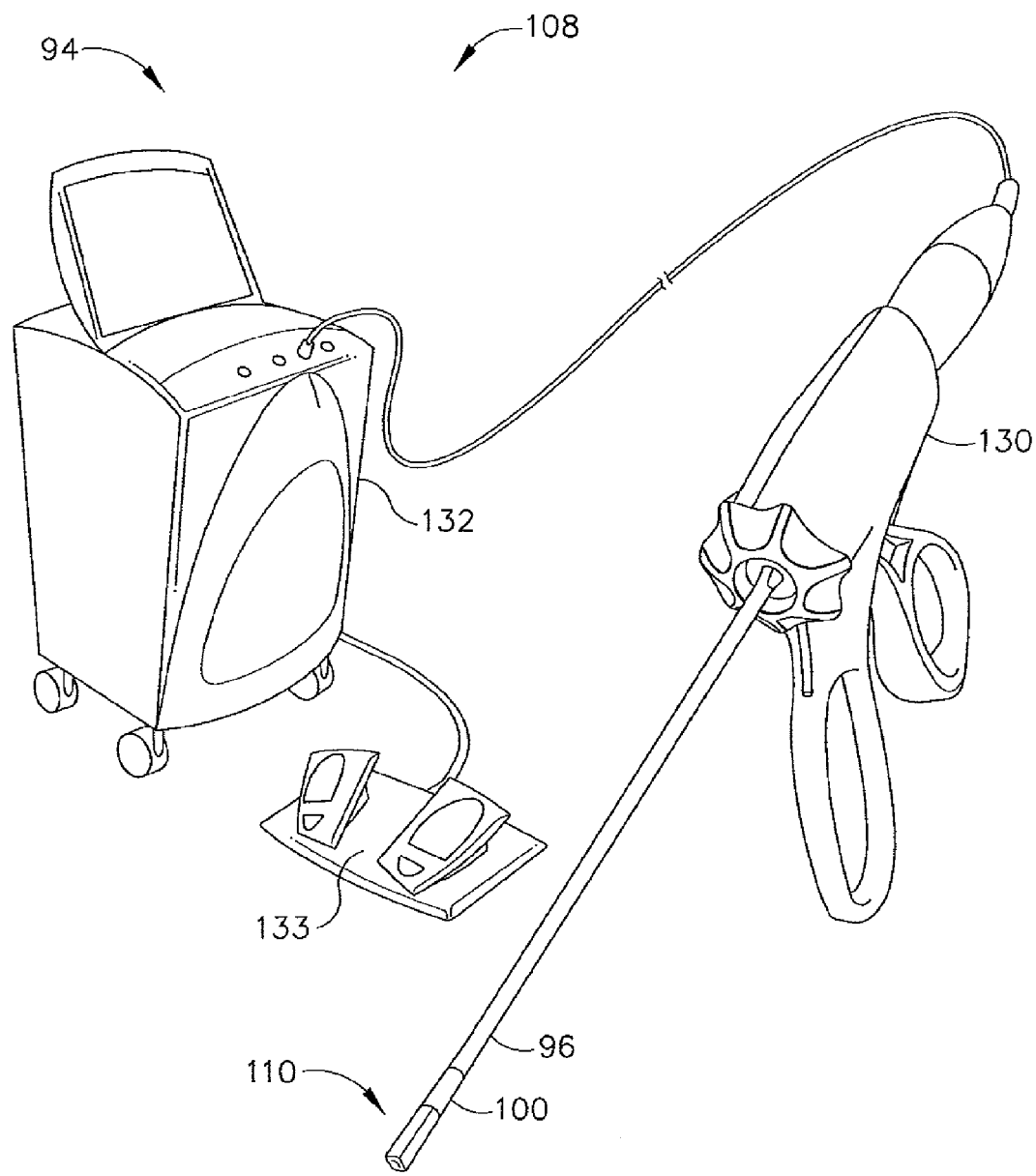
FIG. 9 is a perspective view of a third embodiment of the present invention showing an ultrasound medical system which includes flexible fingers, wherein each finger includes an ultrasound transducer.
Figure 10:
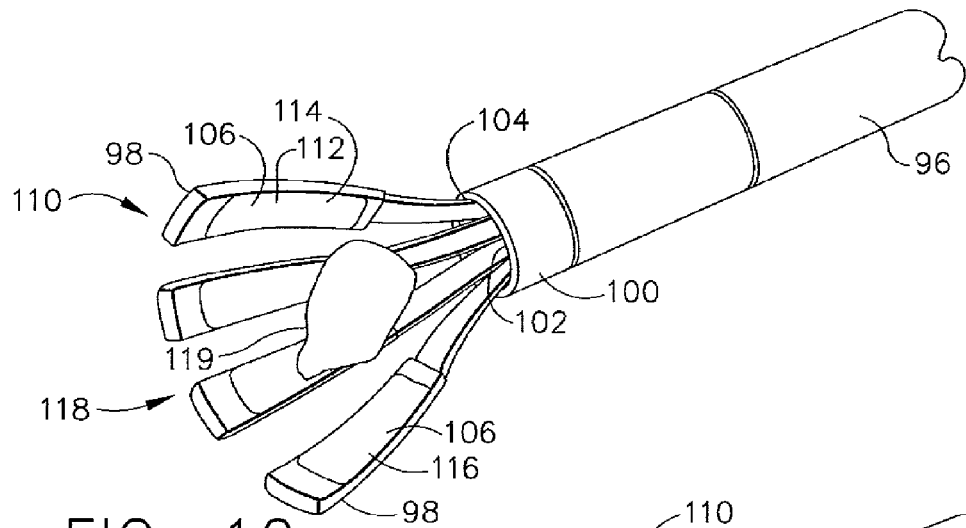
FIG. 10 is an enlarged view of the tube and the flexible fingers of the ultrasound medical system of FIG. 9 showing the flexible fingers in a deployed fan-like state.
Figure 11:
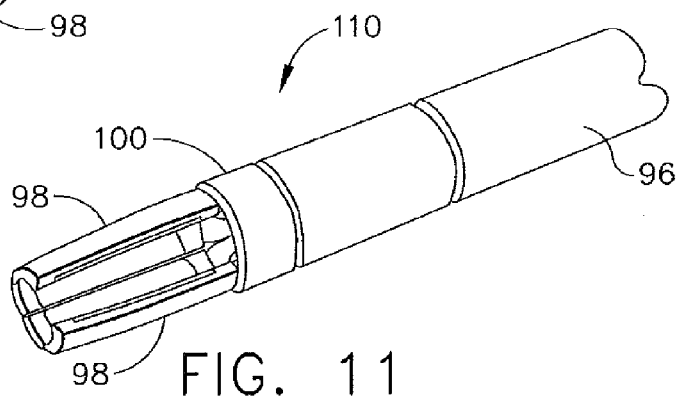
FIG. 11 is a view of the flexible fingers of FIG. 10 shown in a stowed state.

Referring to the drawings, FIGS. 9-11 illustrate a third embodiment of the present invention. A first expression of the third embodiment of the present invention is for an ultrasound medical system 94 including a tube 96 and a plurality of resiliently flexible fingers 98. The tube 96 has a distal end 100 insertable into a patient and has a lumen 102 with a distal opening 104. The fingers 98 are extendable out of the distal opening 104 of the lumen 102 creating a deployed state (seen in FIG. 10) and which are at-least-partially retractable into the distal opening 104 of the lumen 102 creating a stowed state (seen in FIG. 11). Each finger 98 includes an ultrasound transducer 106. The distance between the ultrasound transducers 106 of adjacent fingers 98 is greater in the deployed state than in the stowed state. It is noted that an ultrasound medical system is a medical system which at least provides ultrasound imaging or ultrasound medical treatment of a patient.

Advantages of the tube and extendable/retractable flexible-finger array arrangement include, when the transducers are ultrasound medical-treatment transducers having a common focal zone in the deployed state, providing faster medical treatment times by allowing for more transducer ultrasound-emitting surface area which can be simply stowed into a compact shape for transport within a patient to and from the site of patient tissue receiving ultrasound medical treatment.

In one variation, the fingers 98 are only partially retracted into the distal opening 104 of the lumen 102 in the stowed state (as seen in FIG. 11). In another variation, not shown, the fingers 98 are completely retracted into the distal opening 104 of the lumen 102 in the stowed state. By the fingers 98 being extendable out of the distal opening 104 of the lumen 102 creating the deployed state and being at-least-partially retractable into the distal opening 104 of the lumen 102 creating the stowed state means the fingers 98 protrude more out of the distal opening 104 of the lumen 102 in the extended state than (if at all) in the stowed state. Mechanisms, not shown, for remotely extending and retracting fingers in a tube include, without limitation, a common shaft attached to the proximal ends of the fingers, disposed in the lumen of the tube, and spring-biased to move forward upon squeezing of a handpiece and to return backward upon relaxing of the handpiece, as is within the ordinary level of skill of the artisan. In one modification, the distal opening 104 of the lumen 102 coincides with the distal end 100 of the tube 96. In another modification, not shown, the distal opening of the lumen is spaced apart from the distal end of the tube. In one implementation, the distal opening 104 of the lumen 102 faces in the same direction as the distal end 100 of the tube 96. Other implementations are left to the artisan, such as, without limitation, the distal opening of the lumen facing perpendicular to the distal end of the tube. In one example, at least one of the transducers 106 is an ultrasound imaging transducer. In the same or a different example, at least one of the transducers 106 is an ultrasound medical-treatment transducer. In the same or a different example, at least one of the transducers 106 is an ultrasound imaging and medical-treatment transducer.

A second expression of the third embodiment is for an ultrasound medical treatment system 108 including a tube 96 and including an end effector 110 having a plurality of fingers 98. The tube 96 has a distal end 100 insertable into a patient and has a lumen 102 with a distal opening 104. The fingers 98 are extendable out of the distal opening 104 of the lumen 102 creating a deployed state (seen in FIG. 10) and are at-least-partially retractable into the distal opening 104 of the lumen 102 creating a stowed state (seen in FIG. 11). Each finger 98 includes an ultrasound medical-treatment transducer 112. The distance between the ultrasound medical-treatment transducers 112 of adjacent fingers 98 is greater in the deployed state than in the stowed state.

A third expression of the third embodiment is for an ultrasound medical treatment system 108 including a tube 96 and including an end effector 110 having a plurality of fingers 98. The tube 96 has a distal end 100 insertable into a patient and has a lumen 102 with a distal opening 104. The fingers 98 are extendable out of the distal opening 104 of the lumen 102 creating a deployed state (seen in FIG. 10) and are at-least-partially retractable into the distal opening 104 of the lumen 102 creating a stowed state (seen in FIG. 11). Each finger 98 includes an ultrasound imaging and medical-treatment transducer 114. The distance between the ultrasound imaging and medical-treatment transducers 114 of adjacent fingers 98 is greater in the deployed state than in the stowed state.

It is noted that the variations, modifications, and implementations, etc. previously discussed for the first expression of the third embodiment are equally applicable to the second and third expressions of the third embodiment.

Figure 12:
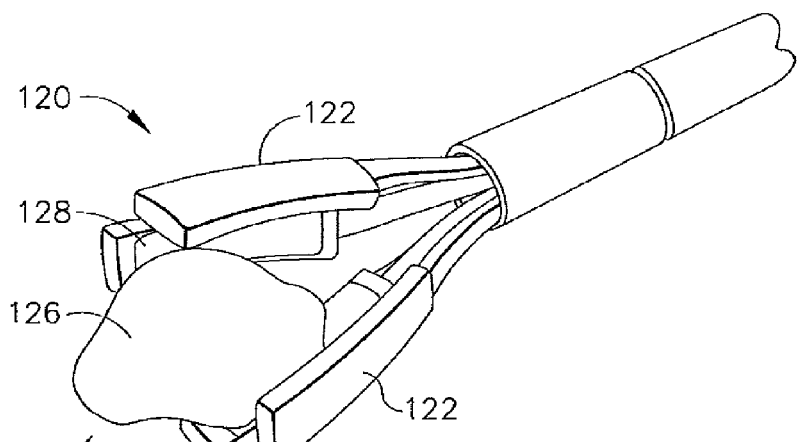
FIG. 12 is a perspective view of an alternate flexible finger arrangement which can be used in the ultrasound medical system of FIG. 9, showing the flexible fingers in a deployed claw-like state surrounding patient tissue.

In one example of the first, second and third expressions of the third embodiment, the transducers 106, 112 and 114 each have an ultrasound-emitting concave surface 116. In another example, not shown, the transducers have a planar ultrasound-emitting surface. In one arrangement, each concave surface 116 is concave as one moves along the corresponding finger 98 (as best seen in FIG. 10). In another arrangement, not shown, each concave surface is concave as one moves across the corresponding finger or is concave as one moves both along and across the corresponding finger (such as, for example, with a hemispherically-concave surface). In one design, the concave surfaces 116 together have a substantially common focal zone when the fingers 98 are in the deployed state. The end effector 110 is seen with its fingers 98 facing the patient tissue 119 in FIG. 10. In another design, not shown, the focal zones are not common. In one configuration, the fingers 98 define an open-hand finger array 118 in the deployed state. An alternate flexible finger arrangement in the form of a substitute end effector 120 is shown in FIG. 12, wherein the fingers 122 define a clawed-hand finger array 124 in the deployed state. The substitute end effector 120 is seen with its fingers 122 surrounding the patient tissue 126 for imaging and/or medical treatment by the ultrasound transducers 128 in FIG. 12. In other transducer arrangements, not shown, one or more or all of the ultrasound transducers face outward rather than facing inward.

In the same or another example of the first, second and third expressions of the third embodiment, the fingers 98 are at least four in number. In the same or yet another example of the second and third expressions of the third embodiment, the end effector 110 (as well as the substitute end effector 120) is an open-surgery end effector, an endoscopic end effector, a laparoscopic end effector (as shown in FIG. 9), a catheter end effector (such as, but not limited to, an intravascular catheter end effector), or a needle end effector, as can be appreciated by those skilled in the art.

In one enablement, as shown in FIG. 9, the ultrasound medical treatment system 108 also includes a handpiece 130 operatively connected to the end effector 110 and to an ultrasound controller 132 operatively connected to a foot-pedal power switch 133, as can be appreciated by those skilled in the art.

Faceted Ultrasound Medical Transducer Assembly

Figure 13:
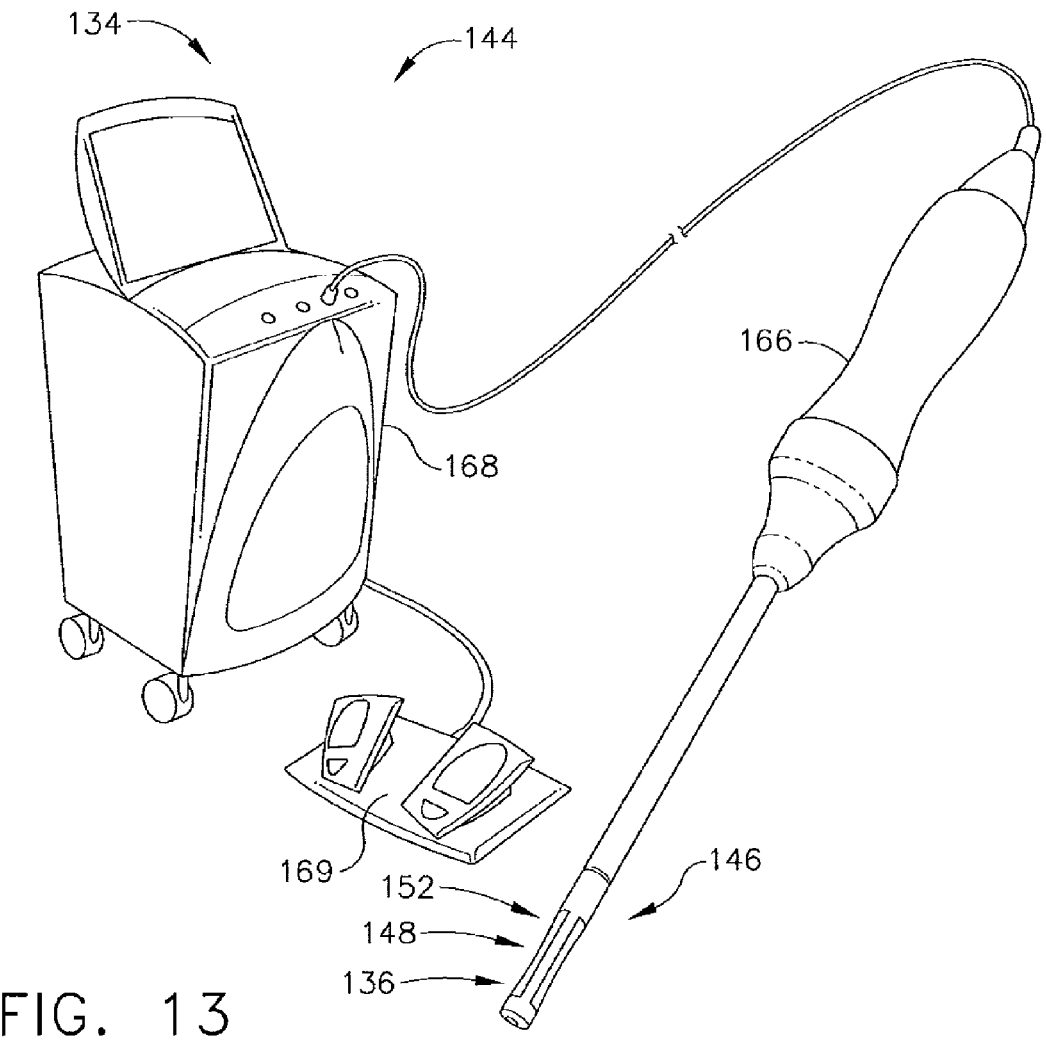
FIG. 13 is a perspective view of a fourth embodiment of the present invention showing an ultrasound medical system which includes an ultrasound transducer assembly which includes at least two ultrasound transducers.
Figure 14:
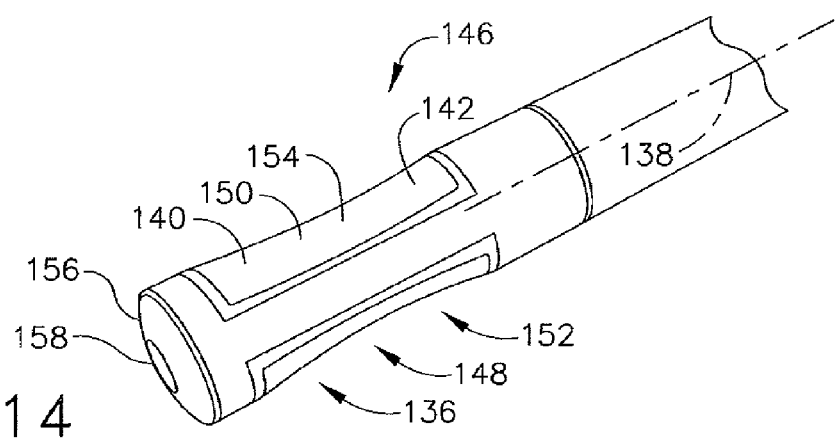
FIG. 14 is an enlarged view of the ultrasound transducer assembly of the ultrasound medical system of FIG. 13.
Figure 15:
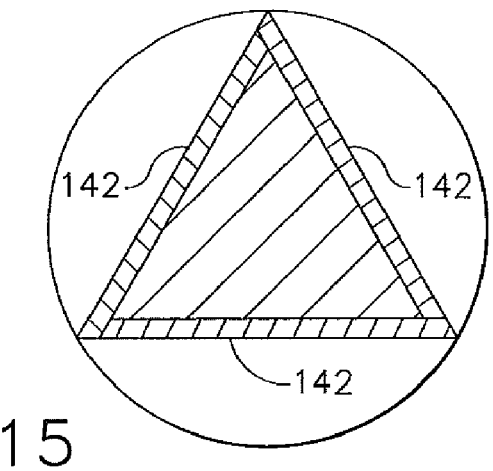
FIG. 15 is a cross-sectional view of the transducer assembly of FIG. 14.

A fourth embodiment of the present invention is shown in FIGS. 13-15. A first expression of the fourth embodiment of the present invention is for an ultrasound medical system 134 including an ultrasound transducer assembly 136 insertable into a patient. The ultrasound transducer assembly 136 has a longitudinal axis 138. The ultrasound transducer assembly 136 includes a plurality P of ultrasound transducers 140. Each transducer 140 has an ultrasound-emitting surface 142 oriented at an angle of substantially 360/P degrees apart from the ultrasound-emitting surface 142 of an adjacent transducer 140 when viewed in a cross section (see FIG. 15) of the transducer assembly 136 taken by a cutting plane which is perpendicular to the longitudinal axis 138.

Advantages of such a transducer configuration include, in one example, providing directed or focused medical-treatment ultrasound which is not possible with a cylindrical ultrasound transducer, as can be appreciated by those skilled in the art.

It is noted that an ultrasound transducer assembly 136 insertable into a patient is an ultrasound imaging transducer assembly, an ultrasound medical-treatment transducer assembly, or an ultrasound imaging and medical-treatment transducer assembly. An ultrasound imaging transducer assembly has at least one ultrasound imaging transducer, and an ultrasound medical-treatment transducer assembly has at least one ultrasound medical-treatment transducer. An ultrasound imaging and medical-treatment transducer assembly has at least one ultrasound imaging transducer and at least one ultrasound medical-treatment transducer or has at least one ultrasound imaging and medical-treatment transducer.

A second expression of the fourth embodiment of the present invention is for an ultrasound medical-treatment system 144 including an end effector 146 insertable into a patient. The end effector 146 includes an ultrasound medical-treatment transducer assembly 148. The ultrasound medical-treatment transducer assembly 148 has a longitudinal axis 138. The ultrasound medical-treatment transducer assembly 148 includes a plurality P of ultrasound medical-treatment transducers 150. Each transducer 150 has an ultrasound-emitting surface 142 which faces away from the longitudinal axis 138 and which is oriented at an angle of substantially 360/P degrees apart from the ultrasound-emitting surface 142 of an adjacent transducer 150 when viewed in a cross section (see FIG. 15) of the transducer assembly 148 taken by a cutting plane which is perpendicular to the longitudinal axis 138. In one example, at least one of the ultrasound medical-treatment transducers 150 is also adapted for ultrasound imaging.

A fourth method of the present invention is for ultrasound medical treatment of a patient and uses the ultrasound medical treatment system 144 as previously described in the second expression of the fourth embodiment. The fourth method includes steps a) through b). Step a) includes inserting the end effector 146 into the liver of the patient. Step b) includes medically treating a lesion in the liver with ultrasound from the ultrasound medical-treatment transducer assembly 148. In one example, step a) interstially inserts the end effector 146 into the lesion. In another example, step a) endoscopically inserts the end effector 146 into the liver through the hepatobiliary duct system.

A third expression of the fourth embodiment of the present invention is for an ultrasound medical treatment system 144 including an end effector 146 insertable into a patient. The end effector 146 includes an ultrasound imaging and medical-treatment transducer assembly 152. The ultrasound imaging and medical-treatment transducer assembly 152 has a longitudinal axis 138. The ultrasound imaging and medical-treatment transducer assembly 152 includes a plurality P of ultrasound imaging and medical-treatment transducers 154. Each transducer 154 has an ultrasound-emitting surface 142 which faces away from the longitudinal axis 138 and which is oriented at an angle of substantially 360/P degrees apart from the ultrasound-emitting surface 142 of an adjacent transducer 154 when viewed in a cross section (see FIG. 15) of the transducer assembly 152 taken by a cutting plane which is perpendicular to the longitudinal axis 138.

A fifth method of the present invention is for ultrasound medical treatment of a patient and uses the ultrasound medical-treatment system 144 as previously described in the third expression of the fourth embodiment. The fourth method includes steps a) through c). Step a) includes inserting the end effector 146 into the liver of the patient. Step b) includes identifying a lesion in the liver for medical treatment at least in part from ultrasound imaging using the ultrasound imaging and medical-treatment transducer assembly 152. Step c) includes medically treating the lesion with ultrasound from the ultrasound imaging and medical-treatment transducer assembly 152. In one example, step a) interstially inserts the end effector 146 into the lesion. In another example, step a) endoscopically inserts the end effector 146 into the liver through the hepato-biliary duct system.

In one example of the previously-described first, second and third expressions of the fourth embodiment, the transducer assembly 136, 148, and 152 has a distal tip 156 and has a tip transducer 158. In one design, the tip transducer is a forward facing tip transducer. In another design, the tip transducer is a sideways facing tip transducer. In one variation, the tip transducer is an ultrasound imaging tip transducer. In another variation, the tip transducer is an ultrasound medical-treatment tip transducer. In a further variation, the tip transducer is an ultrasound imaging and medical-treatment tip transducer. In an additional variation, the tip transducer is a transponder which emits electromagnetic waves or mechanical waves or both.

In the same or a different example of the previously-described first, second and third expressions of the third embodiment, each ultrasound-emitting surface 142 is substantially straight when viewed in the cross section, as seen in FIG. 15. In one variation, as seen in FIG. 14, each ultrasound-emitting surface 142 has a substantially concave shape as one moves along the ultrasound-emitting surface 142 in a direction parallel to the longitudinal axis 138, and each ultrasound-emitting surface 142 has a focal zone. In a first alternate transducer arrangement seen FIG. 16, each ultrasound-emitting surface 162 has a substantially planar shape. In a second alternate transducer arrangement seen in FIG. 17, each ultrasound-emitting surface 164 has a substantially concave shape when viewed in the cross section, and each ultrasound-emitting surface 164 has a focal zone. In one modification, each ultrasound-emitting surface 164 also has a substantially concave shape as one moves along the ultrasound-emitting surface 164 in a direction parallel to the longitudinal axis (such as, for example, by the ultrasound-emitting surface 164 having a hemispherically-concave shape). Such ultrasound-emitting surface shapes are equally applicable to any ultrasound transducer mentioned in any other embodiment of the invention.

Figure 16:
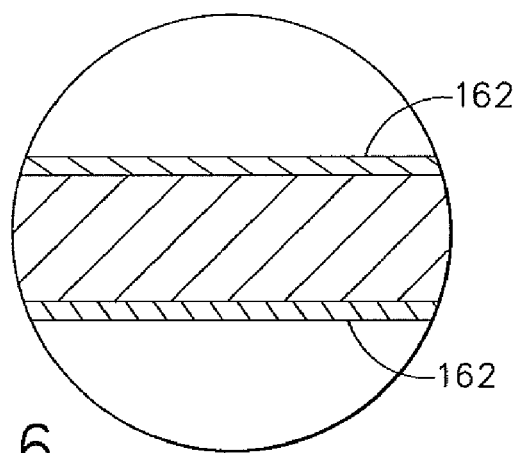
FIG. 16 is a cross-sectional view of a first alternate transducer arrangement which can be used in place of the arrangement of FIG. 15.
Figure 17:
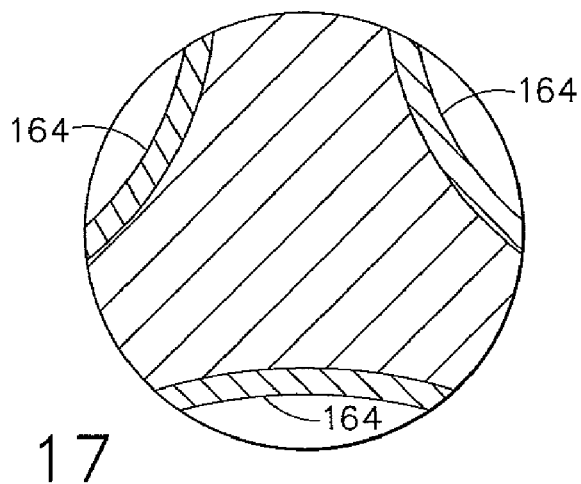
FIG. 17 is a cross-sectional view of a second alternate transducer arrangement which can be used in place of the arrangement of FIG. 15.

In the same or a different example of the previously-described first, second and third expressions of the third embodiment, P is no greater than four. In one variation, P equals three as seen in FIGS. 15 and 17. In another variation, P equals two as seen in FIG. 16.

In the same or a different example of the previously-described second and third expressions of the third embodiment, the end effector 146 is an open-surgery end effector, an endoscopic end effector, a laparoscopic end effector (as shown in FIG. 13), a catheter end effector (such as, but not limited to, an intravascular catheter end effector), or a needle end effector, as can be appreciated by those skilled in the art. In one enablement, as shown in FIG. 13, the ultrasound medical treatment system 144 also includes a handpiece 166 operatively connected to the end effector 146 and to an ultrasound controller 168 operatively connected to a foot-pedal power switch 169, as can be appreciated by the artisan.

Ultrasound Medical Treatment Applications

Excisional and Ultrasound Medical Treatment System

Figure 18:
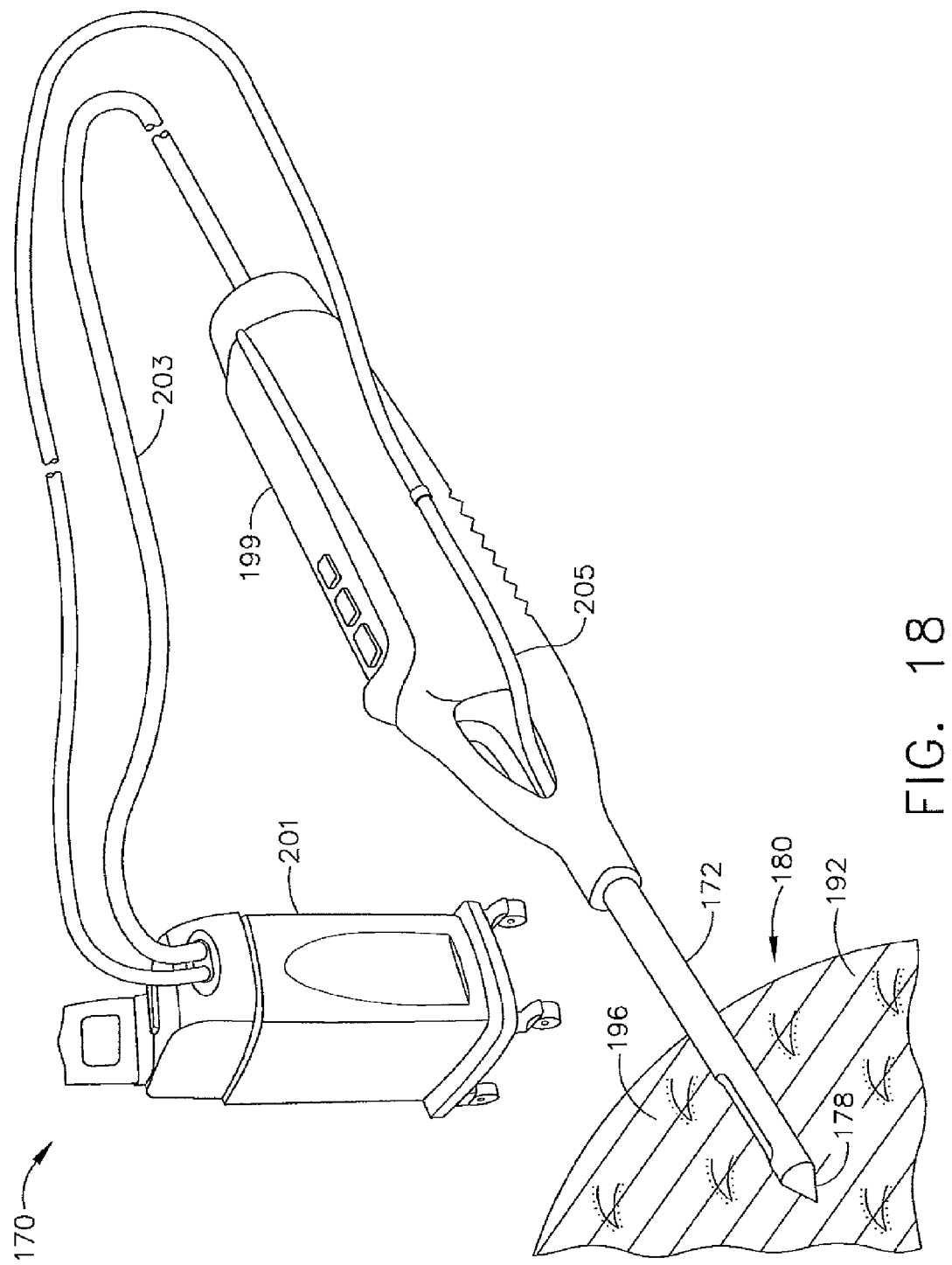
FIG. 18 is a perspective view of a fifth embodiment of the present invention showing an ultrasound medical treatment system which includes a cutting tool and an ultrasound medical-treatment transducer assembly.
Figure 19:
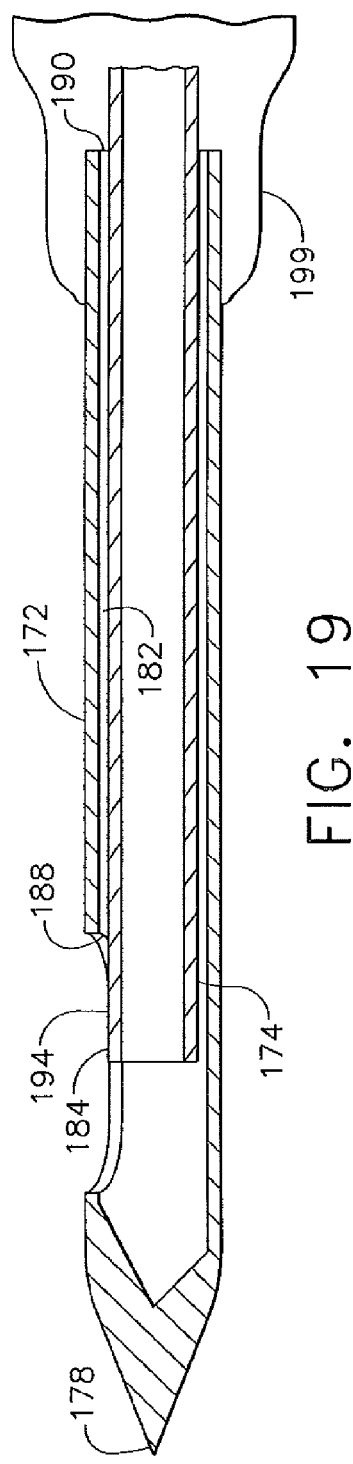
FIG. 19 is an enlarged, cross-sectional view of the tube of FIG. 18 showing a cutting tool that has been introduced into the lumen of the tube.
Figure 20:
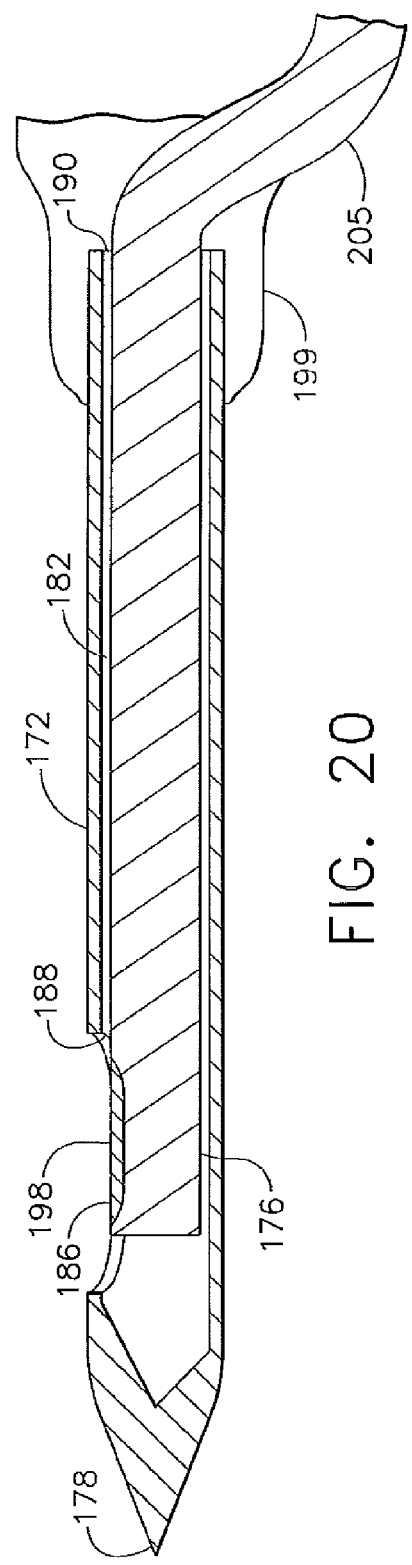
FIG. 20 is an enlarged, cross-sectional view of the tube of FIG. 18 showing an ultrasound medical-treatment transducer assembly that has been introduced into the lumen of the tube.

A fifth embodiment of the present invention is shown in FIGS. 18-20. In a first expression of the fifth embodiment of the present invention, an ultrasound medical treatment system 170 includes a tube 172, a first end effector 174, and a second end effector 176. The tube 172 has a distal end 178 insertable into a patient 180 and has a lumen 182. The first end effector 174 has a cutting tool 184, is introducible into the lumen 182 of the inserted tube 172 from outside the patient 180, and is translatable through the lumen 182 of the inserted tube 172 to inside the patient 180. The second end effector 176 has an ultrasound medical-treatment transducer assembly 186, is introducible into the lumen 182 of the inserted tube 172 from outside the patient 180, and is translatable through the lumen 182 of the inserted tube 172 to inside the patient 180. In one variation, the first and second end effectors are introduced into the lumen through separate openings in the lumen or through separate branch channels leading to the lumen. In another variation, the first and second end effectors are introduced into the lumen through the same opening in the lumen. In one modification, a lumen opening is disposed at the end of the tube. In another modification, a lumen opening is spaced apart from the end of the tube.

A second expression of the fifth embodiment of the present invention is for an ultrasound medical treatment system 170 including a tube 172, a first end effector 174, and a second end effector 176. The tube has a distal end 178 insertable into a patient 180 and has a lumen 182 with a distal opening 188 and a proximal opening 190. The first end effector 174 has a cutting tool 184, is introducible into the proximal opening 190, and is translatable through the lumen 182 to the distal opening 188. The second end effector 176 has an ultrasound medical-treatment transducer assembly 186, is introducible into the proximal opening 190, and is translatable through the lumen 182 to the distal opening 188.

In one example of the first and second expressions of the fifth embodiment of the present invention, the lumen 182 is sized to allow introduction of only one of the first and second end effectors 174 and 176 at a time. In the same or another example, the distal end 178 of the tube 172 is interstitially insertable into patient tissue 192 of the patient 180. In the same or a different example, the cutting tool 184 is a biopsy cutting tool 194 or other excisional cutting tool.

A third expression of the fifth embodiment of the present invention is for an ultrasound medical treatment system 170 including a tube 172, a first end effector 174, and a second end effector 176. The tube 172 has a distal end 178 interstitially insertable into breast tissue 196 of a patient 180 and has a lumen 182 with a distal opening 188 and a proximal opening 190. The first end effector 174 has a biopsy cutting tool 194 (or other excisional cutting tool), is introducible into the proximal opening 190, and is translatable through the lumen 182 to the distal opening 188. The second end effector 176 has an ultrasound medical-treatment transducer assembly 186, is introducible into the proximal opening 190, and is translatable through the lumen 182 to the distal opening 188. The lumen 182 is sized to allow introduction of only one of the first and second end effectors 174 and 176 at a time. In one design, the first end effector also includes a suction mechanism to draw in patient tissue to be biopsied by the biopsy cutting tool 194. In one application, the tube 172 and the first end effector 174 (with the biopsy cutting tool 194 including a suction mechanism) are based on components of a Mammotome® Breast Biopsy System Manufactured by Ethicon Endo-Surgery, Inc. (a Johnson & Johnson Company).

A sixth method of the invention is for ultrasound medical treatment of a patient 180 and uses the ultrasound medical treatment system 170 as previously described in the third expression of the fifth embodiment of the present invention. The sixth method includes steps a) through h). Step a) includes identifying possibly cancerous breast tissue 196 of the patient. Step b) includes interstitially inserting the distal end 178 of the tube 172 into the patient 180 with the distal opening 188 disposed proximate the breast tissue 196 and with the proximal opening 190 disposed outside the patient.

Step c) includes introducing the first end effector 174 into the proximal opening 190 and translating the first end effector 174 through the lumen 182 to the distal opening 188. Step d) includes obtaining a biopsy sample of the breast tissue 196 with the biopsy cutting tool 194. Step e) includes removing the first end effector 174 from the lumen 182, Step f) includes introducing the second end effector 176 into the proximal opening 190 and translating the second end effector 176 through the lumen 182 to the distal opening 188. Step g) includes identifying an area of hemorrhaging in the breast tissue where the biopsy sample was obtained. Step h) includes medically treating the identified area with ultrasound using the transducer assembly 186 to substantially stop the hemorrhaging. In one application, the sixth method of the invention also includes the steps of testing the biopsy sample for cancer and substantially ablating any remaining cancer in the breast tissue with ultrasound using the transducer assembly 186. Advantages of such an ultrasound medical treatment system and method include the ease of obtaining a breast biopsy and the control of hemorrhaging caused by the biopsy procedure coupled together in a minimally invasive manner.

In a fourth expression of the fifth embodiment of the present invention, an ultrasound medical treatment system 170 includes a tube 172, a first end effector 174, and a second end effector 176. The tube 172 has a distal end 178 insertable into a patient 180 and has a lumen 182. The first end effector 174 has a cutting tool 184, is introducible into the lumen 182 of the inserted tube 172 from outside the patient 180, and is translatable through the lumen 182 of the inserted tube 172 to inside the patient 180. The second end effector 176 has an ultrasound imaging and medical-treatment transducer assembly 198, is introducible into the lumen 182 of the inserted tube 172 from outside the patient 180, and is translatable through the lumen 182 of the inserted tube 172 to inside the patient 180. In one variation, the first and second end effectors are introduced into the lumen through separate openings in the lumen or through separate branch channels leading to the lumen. In another variation, the first and second end effectors are introduced into the lumen through the same opening in the lumen. In one modification, a lumen opening is disposed at the end of the tube. In another modification, a lumen opening is spaced apart from the end of the tube.

A fifth expression of the fifth embodiment of the present invention is for an ultrasound medical treatment system 170 including a tube 172, a first end effector 174, and a second end effector 176. The tube has a distal end 178 insertable into a patient 180 and has a lumen 182 with a distal opening 188 and a proximal opening 190. The first end effector 174 has a cutting tool 184, is introducible into the proximal opening 190, and is translatable through the lumen 182 to the distal opening 188. The second end effector 176 has an ultrasound imaging and medical-treatment transducer assembly 198, is introducible into proximal opening 190, and is translatable through the lumen 182 to the distal opening 188.

In one example of the fourth and fifth expressions of the fifth embodiment of the present invention, the lumen 182 is sized to allow introduction of only one of the first and second end effectors 174 and 176 at a time. In the same or another example, the distal end 178 of the tube 172 is interstitially insertable into patient tissue 192 of the patient 180. In the same or a different example, the cutting tool 184 is a biopsy cutting tool 194 or other excisional cutting tool.

A sixth expression of the fifth embodiment of the present invention is for an ultrasound medical treatment system 170 including a tube 172, a first end effector 174, and a second end effector 176. The tube 172 has a distal end 178 interstitially insertable into breast tissue 196 of a patient 180 and has a lumen 182 with a distal opening 188 and a proximal opening 190. The first end effector 174 has a biopsy cutting tool 194 (or other excisional cutting tool), is introducible into the proximal opening 190, and is translatable through the lumen 182 to the distal opening 188. The second end effector 176 has an ultrasound imaging and medical-treatment transducer assembly 196, is introducible into the proximal opening 190, and is translatable through the lumen 182 to the distal opening 188. The lumen 182 is sized to allow introduction of only one of the first and second end effectors 174 and 176 at a time. In one application, the tube 172 and the first end effector 174 (with the biopsy cutting tool 194 including a suction mechanism) are based on components of a Mammotome® Breast Biopsy System manufactured by Ethicon Endo-Surgery, Inc. (a Johnson & Johnson Company).

A seventh method of the invention is for ultrasound medical treatment of a patient 180 and uses the ultrasound medical treatment system 170 as previously described in the sixth expression of the fifth embodiment of the present invention. The seventh method includes steps a) through h). Step a) includes identifying possibly cancerous breast tissue 196 of the patient. Step b) includes interstitially inserting the distal end 178 of the tube 172 into the patient 180 with the distal opening 188 disposed proximate the breast tissue 196 and with the proximal opening 190 disposed outside the patient. Step c) includes introducing the first end effector 174 into the proximal opening 190 and translating the first end effector 174 through the lumen 182 to the distal opening 188. Step d) includes obtaining a biopsy sample of the breast tissue 196 with the biopsy cutting tool 194. Step e) includes removing the first end effector 174 from the lumen 182, Step f) includes introducing the second end effector 176 into the proximal opening 190 and translating the second end effector 176 through the lumen 182 to the distal opening 188. Step g) includes identifying an area of hemorrhaging in the breast tissue where the biopsy sample was obtained from ultrasound imaging using the transducer assembly 198. Step h) includes medically treating the identified area with ultrasound using the transducer assembly 198 to substantially stop the hemorrhaging. In one application, the seventh method of the invention also includes the steps of testing the biopsy sample for cancer and substantially ablating any remaining cancer in the breast tissue with ultrasound using the transducer assembly 198. Advantages of such an ultrasound medical treatment system and method include the ease of obtaining a breast biopsy and the imaging and control of hemorrhaging caused by the biopsy procedure coupled together in a minimally invasive manner.

In one enablement, as shown in FIG. 18, the ultrasound medical treatment system 170 also includes a handpiece 199 which is attached to the tube 172, which contains the first end effector 174 for extending the cutting tool 184 into, and withdrawing it from, the lumen 182, and which is operatively connected to an ultrasound controller 201 via a first cable 203. The second end effector 176, in this enablement, is operatively connected to the ultrasound controller 201 via a second cable 205 and is inserted into the lumen 182 from outside the handpiece 199 as shown in FIG. 18.

Staging Medical Treatment Using Ultrasound

Figure 21:
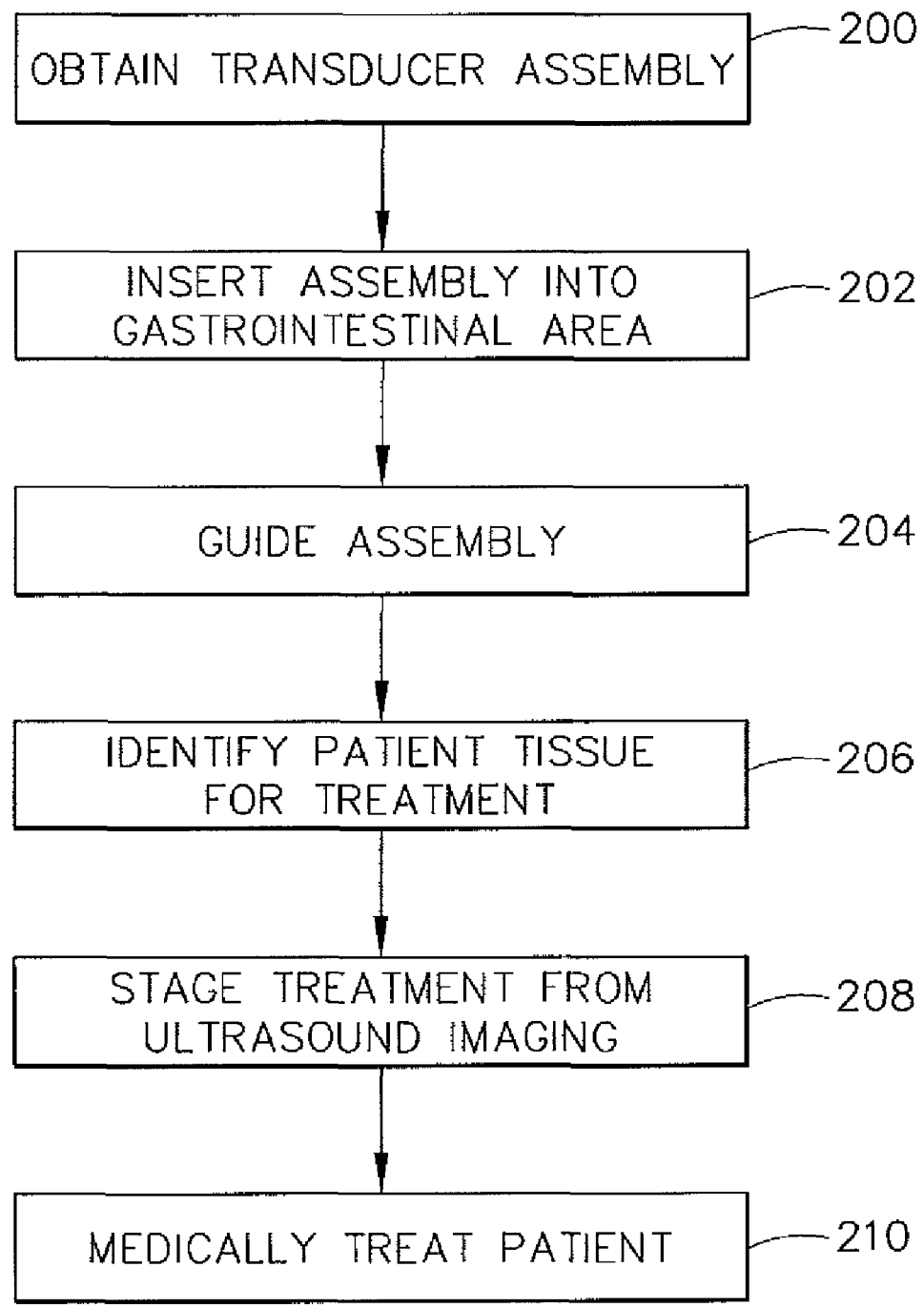
FIG. 21 is a block diagram of an eighth method of the present invention which includes ultrasound staging of medical treatment of patient tissue in the gastrointestinal area.

An eighth method of the invention is shown in block diagram form in FIG. 21 and is for medical treatment of a patient. The eighth method includes steps a) through f). Step a) is labeled "Obtain Transducer Assembly" in block 200 of FIG. 21. Step a) includes obtaining an ultrasound imaging transducer assembly. Step b) is labeled "Insert Assembly Into Gastrointestinal Area" in block 202 of FIG. 21. Step b) includes inserting the transducer assembly into a gastrointestinal area of the patient. Step c) is labeled "Guide Assembly" in block 204 of FIG. 21. Step c) includes guiding the transducer assembly within the gastrointestinal area. Step d) is labeled "Identify Patient Tissue For Treatment" in block 206 of FIG. 21. Step d) includes identifying patient tissue in the gastrointestinal area for medical treatment. Step e) is labeled "Stage Treatment From Ultrasound Imaging" in block 208 of FIG. 21. Step e) includes staging the medical treatment from ultrasound imaging using the transducer assembly. Step f) is labeled as "Medically Treat Patient" in block 210 of FIG. 21. Step f) includes medically treating the patient tissue according to the staging of step e). It is pointed out that in the eighth method the medical treatment need not include ultrasound medical treatment with the transducer assembly used for staging and/or need not include ultrasound medical treatment with any other ultrasound transducer assembly. In one procedure depending on the pathology size and site, a first transducer assembly is used endoscopically to stage the medical treatment in step e) and a second transducer assembly is used laparoscopically to medically treat the patient tissue with ultrasound in step f). In one variation, the first transducer assembly is used laparoscopically to stage the medical treatment in step e) and the second transducer assembly is used endoscopically to medically treat the patient tissue with ultrasound in step f). In another procedure, the medical treatment in step f) is radio-frequency, laser, microwave, or chemical ablation medical treatment. Other types of medical treatment are left to the artisan.

It is noted that the gastrointestinal (GI) area of a human patient includes, without limitation, the esophagus and the stomach of the upper GI area and the rectum and the colon of the lower GI area. It further is noted that the liver is also considered to be in the GI area for purposes of this method.

By "staging the medical treatment from ultrasound imaging" is meant at least using ultrasound images to determine the three-dimensional size and shape of the patient tissue that is to receive medical treatment. For example, and without limitation, upper and lower GI tumors can be visualized with high frequency (6-30 MHz) ultrasound imaging using a cylindrical, side-firing, or half-convex ultrasound array or single-element transducer introduced endoscopically into the GI tract. All layers of the GI tract can be visualized including all layers of the esophagus, stomach, duodenum, colon, etc. In one procedure, a three-dimensional representation of the GI structures is created by collating a series of two-dimensional scans generated by axially advancing the ultrasound transducer. Any neoplastic growth, its morphological characteristics, as well as the tumor's size and shape can easily be determined from the three-dimensional representation.

Advantages of such medical-treatment staging from ultrasound imaging include, in one example, providing a non-invasive medical-treatment staging technique which has greater resolution and which is more practical compared to conventional extracorporeal medical-treatment staging techniques such as using x-rays or MRI imaging or compared to using conventional endoscopic optical techniques.

A ninth method of the invention is for ultrasound medical treatment of a patient and includes steps a) through f). The ninth method uses the same block diagram of FIG. 21 as does the eighth method but with "end effector" replacing "transducer assembly" in block 200 and with "end effector" replacing "assembly" in blocks 202 and 204. Step a) includes obtaining an end effector having an ultrasound imaging and medical-treatment transducer assembly. Step b) includes inserting the end effector into a gastrointestinal area of the patient. Step c) includes guiding the transducer assembly within the gastrointestinal area. Step d) includes identifying patient tissue in the gastrointestinal area for medical treatment. Step e) includes staging the medical treatment from ultrasound imaging using the transducer assembly. Step f) includes medically treating the patient tissue with ultrasound using the transducer assembly according to the staging of step e).

A tenth method of the invention is for ultrasound medical treatment of a patient and includes steps a) through f). The tenth method uses the same block diagram of FIG. 21 as does the eighth method but with "end effector" replacing "transducer assembly" in block 200 and with "end effector" replacing "assembly" in blocks 202 and 204. Step a) includes obtaining an end effector having an ultrasound imaging and medical-treatment transducer assembly. Step b) includes inserting the end effector into a gastrointestinal area of the patient. Step c) includes guiding the transducer assembly within the gastrointestinal area. Step d) includes identifying patient tissue in the gastrointestinal area for medical treatment at least in part from ultrasound imaging using the transducer assembly. Step e) includes staging the medical treatment from ultrasound imaging using the transducer assembly. Step f) includes medically treating the patient tissue with ultrasound using the transducer assembly according to the staging of step e). In one procedure, large GI tumors are staged through a laparoscopic access to the GI area, whereby the tumors are identified, staged and treated using an end effector having an ultrasound imaging and medical-treatment transducer assembly.

In one example of the ninth and tenth methods of the invention, the patient tissue is gastroesophageal tissue containing a lesion, and step f) ultrasonically substantially ablates the lesion. In one modification, the gastroesophageal tissue contains a blood vessel supplying blood to the lesion, and step f) ultrasonically treats the blood vessel to substantially stop the supply of blood to the lesion from the blood vessel.

In another example of the ninth and tenth methods of the invention, the patient tissue is liver tissue containing a lesion and a blood vessel supplying blood to the lesion, and step f) ultrasonically treats the blood vessel to substantially stop the supply of blood to the lesion from the blood vessel.

In an additional example of the ninth and tenth methods of the invention, the patient tissue is liver tissue containing a lesion, and step f) ultrasonically substantially ablates the lesion. In one modification, the liver tissue contains a blood vessel supplying blood to the lesion, and step f) also ultrasonically treats the blood vessel to substantially stop the supply of blood to the lesion from the blood vessel. In one procedure, an end effector having an ultrasound imaging and medical-treatment transducer assembly is introduced endoscopically into the GI tract, is advanced retrogradely through the ampulla of Vater up the common bile duct, and is advanced further into the hepatic duct system where liver parenchyma requiring medical treatment (such as cholangiocarcinomas) are identified, staged, and treated using the end effector.

Treatment of Lung Lesions Using Ultrasound

Figure 22:
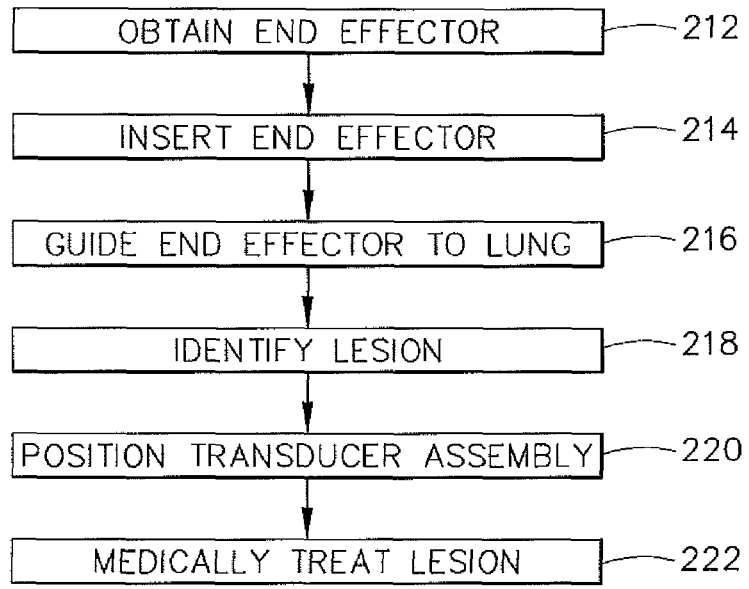
FIG. 22 is a block diagram of an eleventh method of the present invention which includes ultrasound medical treatment of a lesion on or in the lung of a patient.

An eleventh method of the invention is shown in block diagram form in FIG. 22 and is for ultrasound medical treatment of a patient. The eleventh method includes steps a) through f). Step a) is labeled "Obtain End Effector" in block 212 of FIG. 22. Step a) includes obtaining an end effector having an ultrasound medical-treatment transducer assembly. Step b) is labeled "Insert End Effector" in block 214 of FIG. 22. Step b) includes inserting the end effector into the patient. Step c) is labeled "Guide End Effector To Lung" in block 216 of FIG. 22. Step c) includes guiding the end effector within the patient to a lung of the patient. Step d) is labeled "Identify Lesion" in block 218 of FIG. 22. Step d) includes identifying a lesion on or in the lung for medical treatment. Step e) is labeled "Position Transducer Assembly" in block 220 of FIG. 22. Step e) includes positioning the transducer assembly on or in the lesion. Step f) is labeled "Medically Treat Lesion" in block 222 of FIG. 22. Step f) includes medically treating the lesion with ultrasound using the transducer assembly.

A twelfth method of the invention is for ultrasound medical treatment of a patient and includes steps a) through f). The twelfth method uses the same block diagram of FIG. 22 as does the eleventh method. Step a) includes obtaining an end effector having an ultrasound imaging and medical-treatment transducer assembly. Step b) includes inserting the end effector into the patient. Step c) includes guiding the end effector within the patient to a lung of the patient. Step d) includes identifying a lesion on or in the lung for medical treatment at least in part from ultrasound imaging using the transducer assembly. Step e) includes positioning the transducer assembly on or in the lesion. Step f) includes medically treating the lesion with ultrasound using the transducer assembly.

In one example of the eleventh and twelfth methods, step f) ultrasonically substantially ablates the lesion. In one application, the end effector is an endoscopic end effector and step b) transbronchial-endoscopically inserts the end effector into the patient. In another application, the end effector is a needle end effector and step b) interstitially inserts the end effector into the patient. In one implementation, step e) positions the transducer assembly on the lesion. In another implementation, step e) positions the transducer assembly in the lesion. In one practice of the eleventh and twelfth methods, step c) a bronchoscope is used to guide the end effector to a lung of the patient.

Ultrasound medical treatment of the lung has conventionally been avoided because such ultrasound is prevented from reaching a lesion within the lung by the alveoli of the lung which contain air which reflect back most of the ultrasound preventing the ultrasound from effectively penetrating the lung to the lesion. Using higher power ultrasound for effective penetration of the lung to reach the lesion would injure or destroy the alveoli which are needed for breathing. Applicants theorized that positioning the ultrasound transducer on or in a lesion of the lung would allow ultrasound medical treatment of the lesion (such as a tumor or an infarct) without injury to the alveoli. It is noted that Applicants' method is applicable to surface lesions as well as non-surface lesions. Advantages of Applicants' eleventh and twelfth methods for ultrasound medical treatment include, in one example, the destruction of lung cancer lesions in cases which otherwise would be inoperable or incurable.

Ultrasound-Based Occlusive Procedure for Medical Treatment

Figure 23:
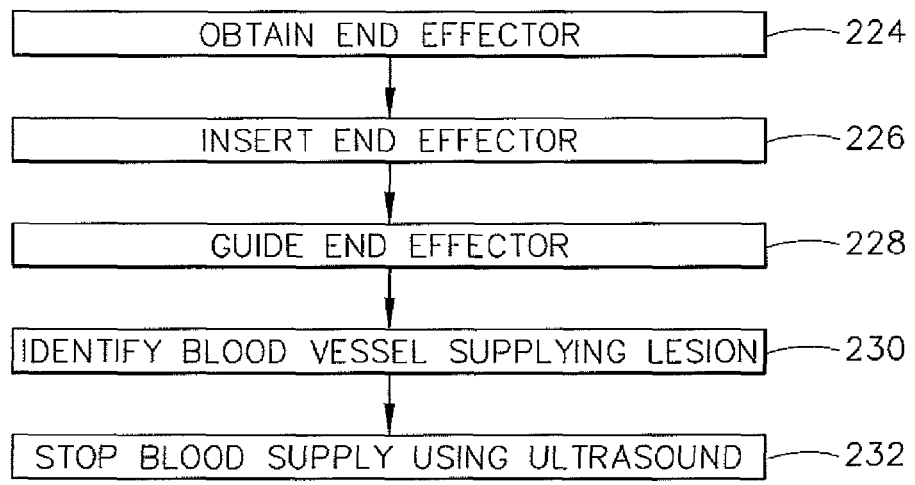
FIG. 23 is a block diagram of a thirteenth method of the present invention which includes ultrasound medical treatment of a blood vessel to stop the supply of blood to a lesion from the blood vessel.

A thirteenth method of the invention is shown in block diagram form in FIG. 23 and is for ultrasound medical treatment of a patient. The thirteenth method includes steps a) through e). Step a) is labeled "Obtain End Effector" in block 224 of FIG. 23. Step a) includes obtaining an end effector having an ultrasound medical-treatment transducer assembly. Step b) is labeled "Insert End Effector" in block 226 of FIG. 23. Step b) includes inserting the end effector into the patient. Step c) is labeled "Guide End Effector" in block 228 of FIG. 23. Step c) includes guiding the end effector within the patient to a region of patient tissue containing a lesion. Step d) is labeled "Identify Blood Vessel Supplying Lesion" in block 230 of FIG. 23. Step d) includes identifying a blood vessel in the region which supplies blood to the lesion. Step e) is labeled "Stop Blood Supply Using Ultrasound" in block 232 of FIG. 23. Step e) includes medically treating the blood vessel with ultrasound from the transducer assembly to substantially seal the blood vessel to stop the supply of blood to the lesion from the blood vessel. One implementation of the thirteenth method of the invention also includes the step of medically treating the lesion with ultrasound from the transducer assembly to substantially ablate the lesion.

A fourteenth method of the invention is for ultrasound medical treatment of a patient and includes steps a) through g). The fourteenth method is similar to the thirteenth method. Step a) includes obtaining an end effector having an ultrasound imaging and medical-treatment transducer assembly. Step b) includes inserting the end effector into the patient. Step c) includes guiding the end effector within the patient to a region of patient tissue containing a lesion. Step d) includes identifying the lesion at least in part from ultrasound imaging using the transducer assembly. Step e) includes identifying a blood vessel in the region which supplies blood to the lesion from ultrasound imaging using the transducer assembly. Step f) includes medically treating the blood vessel with ultrasound from the transducer assembly to substantially seal the blood vessel to substantially stop the supply of blood to the lesion from the blood vessel. Step g) includes medically treating the lesion with ultrasound from the transducer assembly to substantially ablate the lesion. It is noted that Doppler ultrasound imaging alone, gray-scale ultrasound imaging alone, and a combination of Doppler and gray-scale ultrasound imaging are known ultrasound techniques to image blood flow in blood vessels.

In one application of the thirteenth and fourteenth methods, the end effector is an open-surgery end effector. In another application, the end effector is an endoscopic end effector. In a further application, the end effector is a laparoscopic end effector. In an additional application, the end effector is a catheter end effector (such as, but not limited to, an intravascular catheter end effector). In a different application, the end effector is a needle end effector.

A broadened thirteenth method of the invention eliminates the inserting into and guiding within steps of the above-described thirteenth method and includes steps a) through c). Step a) includes obtaining an end effector having an ultrasound medical-treatment transducer assembly. Step b) includes identifying a blood vessel in the patient which supplies blood to a lesion. Step c) includes medically treating the blood vessel with ultrasound from the transducer assembly to substantially seal the blood vessel to substantially stop the supply of blood to the lesion from the blood vessel.

A broadened fourteenth method of the invention eliminates the inserting into and guiding within steps of the above-described fourteenth method and includes steps a) through e). Step a) includes obtaining an end effector having an ultrasound imaging and medical-treatment transducer assembly. Step b) includes identifying a lesion in the patient at least in part from ultrasound imaging using the transducer assembly. Step c) includes identifying a blood vessel which supplies blood to the lesion from ultrasound imaging using the transducer assembly. Step d) includes medically treating the blood vessel with ultrasound from the transducer assembly to substantially seal the blood vessel to substantially stop the supply of blood to the lesion from the blood vessel. Step e) includes medically treating the lesion with ultrasound from the transducer assembly to substantially ablate the lesion.

In one example of the broadened thirteenth and fourteenth methods, the end effector is an extracorporeal end effector. In another example, the end effector is an intracorporeal end effector. In a further example, the end effector can be used in both an extracorporeal mode and in an intracorporeal mode.

Advantages of Applicants' thirteenth and broadened thirteenth methods for ultrasound medical treatment include, in one example, the indirect destruction of cancer lesions by ultrasound hemostasis in blood vessels supplying the cancer lesions in cases which otherwise would be inoperable or incurable because the location of the cancer lesions prevents medical treatment of the lesions themselves.

Advantages of Applicants' fourteenth and broadened fourteenth methods for ultrasound treatment include, in one example, direct destruction of cancer lesions by ultrasound ablation of the cancer lesions together with the indirect destruction of any cancer lesions missed in the ultrasound ablation step by ultrasound hemostasis in blood vessels supplying blood to the missed cancer lesions.

Guiding and Targeting Ultrasound End Effectors

Guiding Ultrasound End Effector for Medical Treatment

Figure 24:
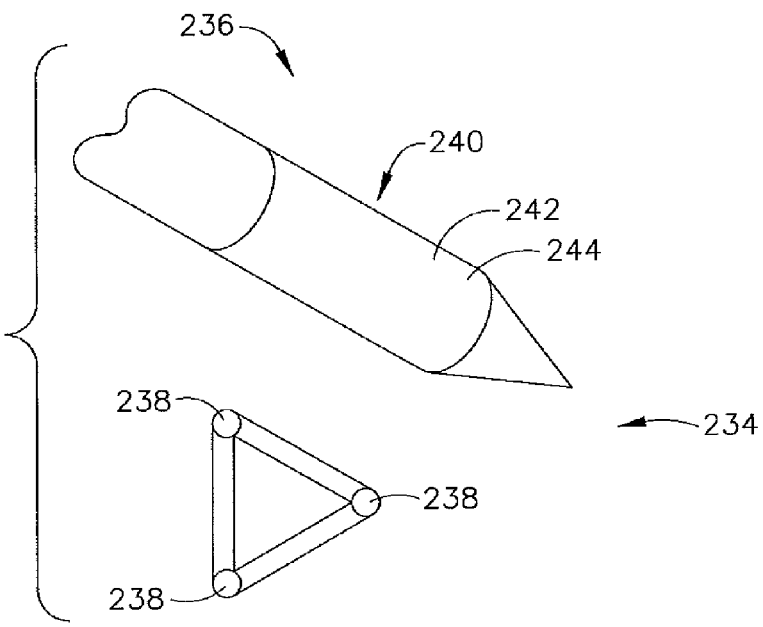
FIG. 24 is a perspective view of a sixth embodiment of the present invention showing a portion of an ultrasound medical treatment system which includes receivers for locating the position of the transducer assembly of the system.

A sixth embodiment of the present invention is shown in FIG. 24. In a first expression of the sixth embodiment of the present invention, an ultrasound medical treatment system 234 (only a portion of which is shown in FIG. 24) includes an end effector 236 and at least three receivers 238. The end effector 236 has a transducer assembly 240 including a transducer 242 having at least one transducer element 244 adapted for emitting medical-treatment ultrasound waves and for emitting mechanical waves. It is noted that the terminology "mechanical waves" includes ultrasound and non-ultrasound compression (acoustic) waves and ultrasound and non-ultrasound shear waves, and that waves include wave pulses. The receivers 238 are spaced apart from the transducer assembly 240, and the receivers 238 are adapted to receive the emitted mechanical waves for use in locating the position of the transducer assembly 240. Conventional methods (including triangulation methods) for locating the position of a transponder emitting waves which are received by three receivers are well known. A second expression of the sixth embodiment is identical to the first expression of the sixth embodiment except that the at-least-one transducer element 244 is also adapted for emitting imaging ultrasound waves. In one variation of the first and second expressions of the sixth embodiment, the end effector and the receivers are disposable outside (including in one modification on) the patient. In another variation, the end effector is insertable into the patient and the receivers are disposable outside (including in one modification on) the patient.

Figure 25:
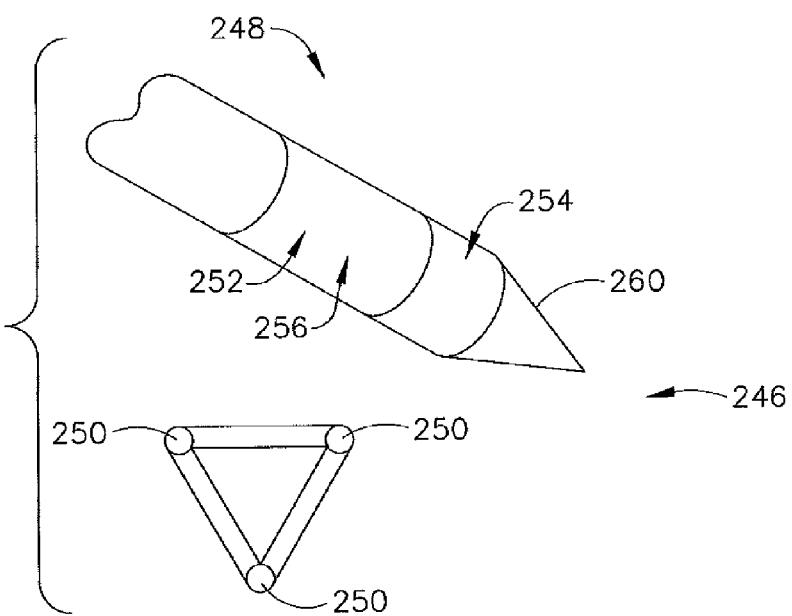
FIG. 25 is a perspective view of a seventh embodiment of the present invention showing a portion of another ultrasound medical treatment system which includes receivers for locating the position of the transponder of the system.

A seventh embodiment of the present invention is shown in FIG. 25. In a first expression of the seventh embodiment of the present invention, an ultrasound medical treatment system 246 (only a portion of which is shown in FIG. 25) includes an end effector 248 and at least three receivers 250. The end effector 248 has an ultrasound medical-treatment transducer assembly 252 and has a transponder 254 The transponder 254 is adapted to emit waves, and the waves include electromagnetic waves or mechanical waves or both. The receivers 250 are spaced apart from the transducer assembly 252, and the receivers 250 are adapted to receive the emitted waves for use in locating the position of the transponder 254. In a second expression of the seventh embodiment, the ultrasound medical-treatment transducer assembly 252 is an ultrasound imaging and medical-treatment transducer assembly 256.

In one application of the first and second expressions of the seventh embodiment, the end effector 248 is insertable into a patient, the transponder 254 is adapted to emit electromagnetic waves, and the receivers 250 are disposable outside the patient. In one variation, the receivers 250 are disposable on the patient. In another application, the end effector is disposable outside (including in one modification on) the patient and the receivers are disposable outside (including in one modification on) the patient.

In one example of the first and second expressions of the seventh embodiment, the end effector 248 is an endoscopic end effector, a laparoscopic end effector, a catheter end effector (such as, but not limited to, an intravascular catheter end effector), or a needle end effector. In one design of the first and second expressions of the seventh embodiment, the end effector 248 has a distal tip 260, and the transponder 254 is disposed at the distal tip 260 of the end effector 248. In one variation, the transducer assembly 252 and 256 is disposed proximate the transponder 254.

A fifteenth method of the invention uses the ultrasound medical treatment system of the first expression of the seventh embodiment and includes steps a) through h). Step a) includes inserting the end effector 248 into the patient. Step b) includes disposing the receivers 250 outside the patient. Step c) includes emitting electromagnetic waves from the transponder 254. Step d) includes receiving the electromagnetic waves with the disposed receivers 250. Step e) includes calculating the position of the transponder 254 from the received electromagnetic waves. Step f) includes guiding the end effector within the patient to a desired location from the calculated position of the transponder 254. Step g) includes, after step f), identifying patient tissue for medical treatment. Step h) includes medically treating the identified patient tissue with ultrasound using the transducer assembly 252.

A sixteenth method of the invention uses the ultrasound medical treatment system of the second expression of the seventh embodiment and includes steps a) through h). Step a) includes inserting the end effector 248 into the patient. Step b) includes disposing the receivers 250 outside the patient. Step c) includes emitting electromagnetic waves from the transponder 254. Step d) includes receiving the electromagnetic waves with the disposed receivers 250. Step e) includes calculating the position of the transponder 254 from the received electromagnetic waves. Step f) includes guiding the end effector within the patient to a desired location from the calculated position of the transponder 254. Step g) includes, after step f), identifying patient tissue for medical treatment at least in part from ultrasound imaging using the transducer assembly 256. Step h) includes medically treating the identified patient tissue with ultrasound using the transducer assembly 256.

A known electromagnetic transponder and three-receiver system for calculating the position of the transponder and for guiding the transponder (which is attached to a heart catheter for monitoring the heart) inside a patient is the CARTO™ EP Navigation System used with a NAVI-STAR® catheter manufactured by Biosense Webster (a Johnson & Johnson Company).

Advantages of an end effector with ultrasound medical treatment and position-location capabilities include, in one example, more accurately guiding the end effector inside a patient to patient tissue for ultrasound medical treatment of the patient tissue.

Method for Aiming Ultrasound for Medical Treatment

Figure 26:
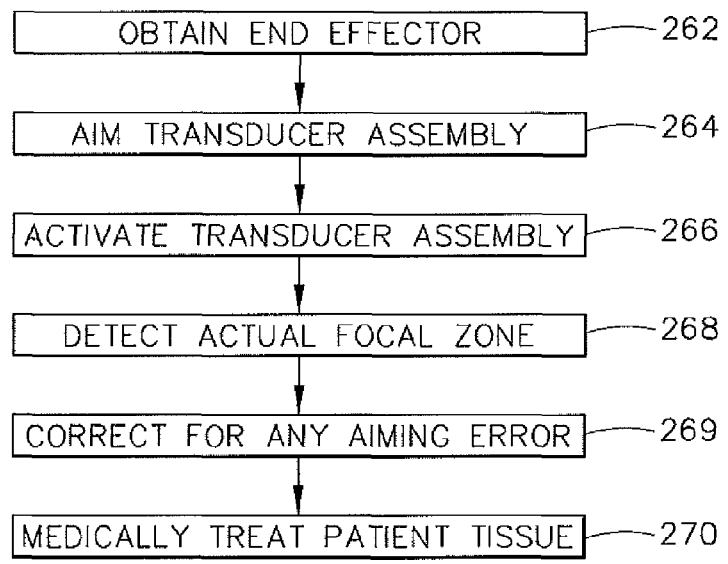
FIG. 26 is a block diagram of a seventeenth method of the present invention which includes aiming the transducer assembly.

A seventeenth method of the invention is shown in block diagram form in FIG. 26 and is for ultrasound medical treatment of a patient. The seventeenth method includes steps a) through f). Step a) is labeled "Obtain End Effector" in block 262 of FIG. 26. Step a) includes obtaining an end effector having an ultrasound medical-treatment transducer assembly. Step b) is labeled "Aim Transducer Assembly" in block 264 of FIG. 26. Step b) includes aiming the transducer assembly to focus ultrasound energy at a desired focal zone of patient tissue. It is noted that, in one example, to aim a transducer assembly means to focus ultrasound energy at a particular distance from the transducer assembly and along a particular direction. Step c) is labeled "Activate Transducer Assembly" in block 266 of FIG. 26. Step c) includes activating the aimed transducer assembly to emit ultrasound energy sufficient to achieve a temperature increase in the patient tissue essentially without medically affecting the patient tissue. Step d) is labeled "Detect Actual Focal Zone" in block 268 of FIG. 26. Step d) includes after step c) detecting, from reflected ultrasound energy, an actual focal zone of patient tissue having a temperature increase. Step e) is labeled "Correct For Any Aiming Error" in block 269 of FIG. 26. Step e) includes correcting for any error between the desired focal zone and the actual focal zone. Step f) is labeled "Medically Treat Patient Tissue" in block 270 of FIG. 26. Step f) includes after step e), medically treating the patient tissue with ultrasound using the transducer assembly. In one application, step d) uses one or more additional ultrasound transducer assemblies, separate from the ultrasound transducer assembly used in steps a) through c) and e) through f), to detect, from reflected ultrasound energy, the actual focal zone. In another application, the same ultrasound transducer assembly is used for steps a) through f). In one example of the seventeenth method, the end effector is an extracorporeal end effector. In another example, the end effector is an intracorporeal end effector. In a further example, the end effector can be used in both an extracorporeal mode and in an intracorporeal mode.

An eighteenth method of the invention is for ultrasound medical treatment of a patient and includes steps a) through f). The eighteenth method uses the same block diagram of FIG. 26 as does the seventeenth method. Step a) includes obtaining an end effector having an ultrasound imaging and medical-treatment transducer assembly. Step b) includes aiming the transducer assembly to focus ultrasound energy at a desired focal zone of patient tissue. Step c) includes activating the aimed transducer assembly to emit ultrasound energy sufficient to achieve a temperature increase in the patient tissue essentially without medically affecting the patient tissue. Step d) includes after step c) detecting, from reflected ultrasound energy using the transducer assembly, an actual focal zone of patient tissue having a temperature increase. Step e) includes correcting for any error between the desired focal zone and the actual focal zone. Step f) includes after step e), medically treating the patient tissue with ultrasound using the transducer assembly. In one example, the end effector is an extracorporeal end effector. In another example, the end effector is an intracorporeal end effector. In a further example, the end effector can be used in both an extracorporeal mode and in an intracorporeal mode.

A nineteenth method of the invention is for ultrasound medical treatment of a patient and includes steps a) through i). The nineteenth method uses the same block diagram of FIG. 26 as does the seventeenth method but with three extra steps added between block 262's step a) and block 264's step b) of the seventeenth method. In the nineteenth method, step a) includes obtaining an end effector having an ultrasound imaging and medical-treatment transducer assembly. Step b) includes inserting the end effector into the patient. Step c) includes guiding the end effector inside the patient. Step d) includes identifying a desired focal zone of patient tissue at least in part from ultrasound imaging using the transducer assembly. Step e) includes aiming the transducer assembly to focus ultrasound energy at the desired focal zone of patient tissue. Step f) includes activating the aimed transducer assembly to emit ultrasound energy sufficient to achieve a temperature increase in the patient tissue essentially without medically affecting the patient tissue. Step g) includes after step f) detecting, from reflected ultrasound energy using the transducer assembly, an actual focal zone of patient tissue having a temperature increase. Step h) includes correcting for any error between the desired focal zone and the actual focal zone. Step i) includes after step h), medically treating the patient tissue with ultrasound using the transducer assembly.

In one example of the seventeenth through nineteenth methods, the end effector is an endoscopic end effector. In another example, the end effector is a laparoscopic end effector. In a further example, the end effector is a catheter end effector (such as, but not limited to, an intravascular catheter end effector). In an additional example, the end effector is a needle end effector.

It is noted that the achieved temperature increase will decrease over time so that the detected temperature increase may not exactly equal the achieved temperature increase. In one implementation of the seventeenth through nineteenth methods, the temperature increase detected in the detecting step is equal substantially to the temperature increase achieved in the activating step. In one application of the seventeenth through nineteenth methods, the detected temperature increase is not greater than about five degrees Celsius. In one variation, the detected temperature increase is not greater than about two degrees Celsius.

It is noted that conventional methods are known to the artisan to convert ultrasound image data into temperature images. In one variation of the seventeenth through nineteenth methods, the correcting step is performed automatically by a feedback control on the same mechanism used to aim the transducer assembly in the aiming step, as can be appreciated by the artisan. As previously noted, mechanisms for aiming an ultrasound medical-treatment transducer assembly include conventional electronic and/or mechanical techniques as are known to those skilled in the art.

Advantages of correcting for any error between the desired and actual focal zones before medical treatment include more precise ultrasound medical treatment of patient tissue. In one example, better targeting maximizes the ablation of a lesion (and any appropriate margin) while minimizing medical treatment of patient tissue outside the lesion (and outside any appropriate margin).

Ultrasound Imaging of Patient Tissue

Ultrasound Feedback in Medically-Treated Patients

Figure 27:
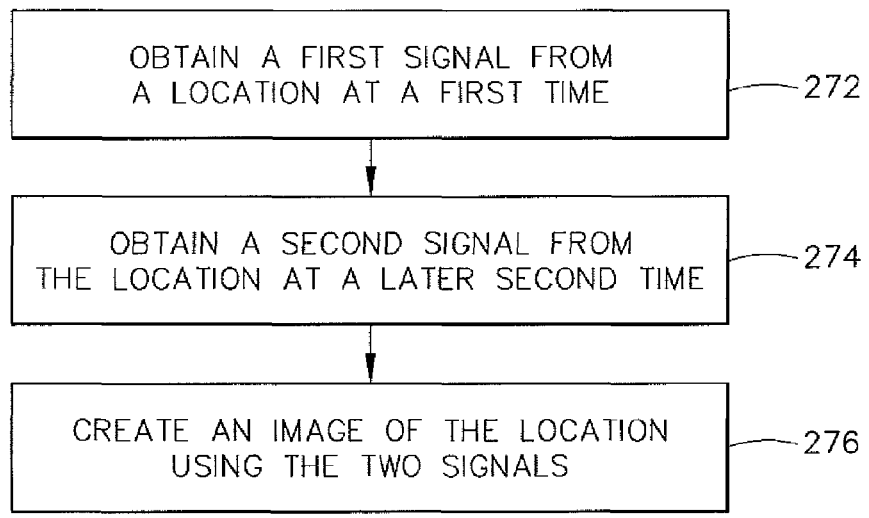
FIG. 27 is a block diagram of a twentieth method of the present invention which includes creating an image after starting medical treatment using an imaging ultrasound wave before medical treatment and an imaging ultrasound wave after starting medical treatment.

A twentieth method of the invention is shown in block diagram form in FIG. 27 and is for ultrasound imaging of patient tissue of a patient. The twentieth method includes steps a) through c). Step a) is labeled "Obtain A First Signal From A Location At A First Time" in block 272 of FIG. 27. Step a) includes obtaining a first signal of a first imaging ultrasound wave which has been reflected back from a location in the patient tissue at a first time. Step b) is labeled "Obtain A Second Signal From The Location At A Later Second Time" in block 274 of FIG. 27. Step b) includes obtaining a second signal of a second imaging ultrasound wave which has been reflected back from the location in the patient tissue at a later second time wherein the patient has received at least some medical treatment by the second time. Step c) is labeled "Create An Image Of The Location Using The Two Signals" in block 276 of FIG. 27. Step c) includes creating an image of the location using the first signal and the second signal. It is understood that the terminology "creating an image" includes, without limitation, creating an image in visual form displayed, for example, on a monitor and creating an image in electronic form which, for example, is used by a computer without being displayed in visual form on a monitor. In one enablement of the twentieth method of the invention, the image of the location is visually displayed at a pixel location on a monitor.

In one example of the twentieth method of the invention, step c) includes creating an image of the location using at least the amplitude of the first signal and the amplitude of the second signal. In one variation, step c) calculates the difference in the amplitudes between the first and second signals. In one modification, step c) uses the calculated amplitude difference and uses one of the amplitudes of one of the first and second signals. In one implementation, step c) calculates the sum of the one amplitude and a function of the calculated amplitude difference. In one illustration for a first signal amplitude of 6 and a second signal amplitude of 7, step c) calculates the amplitude difference, adds the difference to the second signal amplitude creating a processed amplitude of 8, and creates the image of the location using the processed amplitude. Other algorithms for using the amplitude of the first and second signals to enhance any amplitude difference in creating the image of the location after medical treatment are left to the artisan.

In another example of the twentieth method of the invention, step c) includes creating an image of the location using at least the phase of the first signal and the phase of the second signal. In one variation, step c) calculates the difference in the phase between the first and second signals. In one modification, step c) uses the calculated phase difference and uses one of the phases of one of the first and second signals. In one implementation, step c) calculates the sum of the one phase and a function of the calculated phase difference. In one illustration of a first signal phase of 6 degrees and a second signal phase of 7 degrees, step c) calculates the phase difference, adds the difference to the second signal phase creating a processed phase of 8 degrees, and creates the image of the location using the processed phase. Other algorithms for using the phase of the first and second signals to enhance any phase difference in creating the image after medical treatment are left to the artisan.

In an additional example of the twentieth method of the invention, step c) includes creating an image of the location using at least the amplitude and the phase of the first signal and the amplitude and phase of the second signal. In one variation step c) combines the discussions in the previous two paragraphs, as is within the ordinary level of skill of the artisan.

In one application of the twentieth method and examples, etc. thereof, the first signal of step a) has a first frequency (e.g., a first center frequency having a sigma) and the second signal of step b) has a second frequency (e.g., a second center frequency having a sigma) which is different from the first frequency (meaning, for example, that the center frequencies are different). In the same or a different application, the medical treatment is ultrasound medical treatment. In the same or a different application, steps a) through c) are repeated for different locations to image the patient tissue, wherein the image of the patient tissue includes medically-treated locations and medically-untreated locations. In one enablement of the twentieth method of the invention, the image of the patient tissue is visually displayed on a monitor. In another enablement, the image remains as an image map in a computer without being displayed on a monitor. In one extension of the twentieth method, additional signals are obtained between steps a) and b) which are also used in creating the image of the location in step c).

Applicants were the first to realize that changes in patient tissue because of medical treatment of patient tissue, such as ultrasound medical treatment, which affect the amplitude and/or phase of ultrasound imaging signals can be used to enhance the ultrasound image differences of medically-treated patient tissue from surrounding untreated tissue. Applicants have theorized that using different frequencies for the two signals can enhance amplitude and/or phase differences for medically treated and untreated tissue and can be used to enhance the ultrasound image differences of medically-treated patient tissue from surrounding untreated tissue. Advantages of the twentieth method and examples, etc. thereof include, in one application, better ultrasound image contrast between treated and untreated patient tissue providing better monitoring during patient treatment.

Other medical treatments applicable to the twentieth method include, without limitation, other thermal ablation techniques such as radio-frequency, laser, and microwave medical treatments and chemical ablation techniques such as ethanol and chemo-therapeutics (including anti-cancer drugs). Other optional steps in the twentieth method include using signal smoothing techniques, as are known to those skilled in the art.

It is understood that any one or more of the previously-described embodiments, expressions of embodiments, examples, methods, etc. can be combined with any one or more of the other previously-described embodiments, expressions of embodiments, examples, methods, etc. For example, and without limitation, any of the end effectors can be used in any of the methods, any of the transducer arrangements can be used in any of the end effectors, and any appropriate methods can be combined such as combining the seventeenth and twentieth methods, etc.

The foregoing description of several expressions of embodiments and methods of the invention has been presented for purposes of illustration. It is not intended to be exhaustive or to limit the invention to the precise forms and procedures disclosed, and obviously many modifications and variations are possible in light of the above teaching. For example, as would be apparent to those skilled in the art, the disclosures herein of the ultrasonic systems and methods have equal application in robotic assisted surgery taking into account the obvious modifications of the invention to be compatible with such a robotic system. It is intended that the scope of the invention be defined by the claims appended hereto.

What is claimed is:

1. An ultrasound medical treatment system comprising an end effector insertable into a patient, wherein the end effector includes a tissue-retaining device, wherein the tissue-retaining device includes a first tissue-retaining member having an ultrasound imaging and medical-treatment transducer and includes a second tissue-retaining member, and wherein the first and second tissue-retaining members are operatively connected together to retain patient tissue between the first and second tissue retaining members and to release patient tissue so retained, wherein the first tissue-retaining member is a distal end portion of a first tube, wherein a second tube is oriented substantially parallel to the first tube, wherein a first and second link members pivotally attached to the first tissue-retaining member and to the second tube at pivot points creating a hinged parallelogram defined by a proximal portion of the first tissue-retaining member, a distal portion of the second tube, and the first and second link members, and a cable operatively connected to the hinged parallelogram to move the second tissue-retaining member toward and away from the first tissue-retaining member.

2. The ultrasound medical treatment system of claim 1, wherein the retained patient tissue is retained between the transducer and the second tissue-retaining member.

3. The ultrasound medical treatment system of claim 1, wherein the end effector is an open-surgery end effector, an endoscopic end effector, a laparoscopic end effector, a catheter end effector, or a needle end effector.

4. The ultrasound medical treatment system of claim 1, wherein the transducer focuses ultrasound energy.

5. A method for ultrasound medical treatment of a patient using the ultrasound medical treatment system of claim 1 comprising the steps of:
   a) endoscopically inserting the end effector into an ear, nose, or throat of the patient;
   b) guiding the end effector in the patient;
   c) identifying patient tissue for medical treatment at least in part from ultrasound imaging using the transducer;
   d) retaining the identified patient tissue using the tissue-retaining device; and
   e) medically treating the retained patient tissue with ultrasound using the transducer.

6. A method for ultrasound medical treatment of a patient using the ultrasound medical treatment system of claim 1 comprising the steps of:
   a) inserting the end effector into the patient;
   b) retaining an intervertebral disk of the patient with the tissue-retaining device, wherein the intervertebral disk includes tissue; and
   c) medically treating the retained intervertebral disk with ultrasound to shrink the tissue using the transducer.

7. A method for ultrasound medical treatment of a patient using the ultrasound medical treatment system of claim 1 comprising the steps of:
   a) inserting the end effector into the patient;
   b) retaining a joint of the patient with the tissue-retaining device, wherein the joint includes tissue; and
   c) medically treating the retained joint with ultrasound to shrink the tissue using the transducer.

8. The ultrasound medical treatment system of claim 1, wherein the second tissue-retaining member is substantially ultrasonically non-reflective.

9. An ultrasound medical treatment system comprising an end effector insertable into a patient, wherein the end effector includes a tissue-retaining device, wherein the tissue-retaining device includes a first tissue-retaining member having an ultrasound imaging and medical-treatment transducer and includes a second tissue-retaining member having an ultrasound reflector, and wherein the first and second tissue-retaining members are operatively connected together to retain patient tissue between the first and second tissue-retaining members and to release patient tissue so retained, wherein the first tissue-retaining member is a distal end portion of a first tube, wherein a second tube is oriented substantially parallel to the first tube, wherein a first and second link members pivotally attached to the first tissue-retaining member and to the second tube at pivot points creating a hinged parallelogram defined by a proximal portion of the first tissue-retaining member, a distal portion of the second tube, and the first and second link members, wherein the reflector is disposed at a distal portion of the second tissue-retaining member and faces the transducer, and a cable operatively connected to the hinged parallelogram to move the second tissue-retaining member toward and away from the first tissue-retaining member.

10. The ultrasound medical treatment system of claim 9, wherein the retained patient tissue is retained between the transducer and the reflector.

11. The ultrasound medical treatment system of claim 9, wherein the end effector is an open-surgery end effector, an endoscopic end effector, a laparoscopic end effector, a catheter end effector, or a needle end effector.

12. The ultrasound medical treatment system of claim 9, wherein the reflector is disposed to receive ultrasound energy from the transducer and is oriented to reflect the received ultrasound energy back into patient tissue retained by the tissue-retaining device.

13. The ultrasound medical treatment system of claim 12, wherein the transducer and the reflector each focus ultrasound energy.

14. The ultrasound medical treatment system of claim 12, wherein the reflector is oriented to reflect the received ultrasound energy away from the transducer when the patient tissue is retained by the tissue-retaining device.

15. The ultrasound medical treatment system of claim 9, wherein one of the first and second tissue-retaining members is controllably orientatable relative to the other of the first and second tissue-retaining members.

16. The ultrasound medical treatment system of claim 15, wherein the second tissue-retaining member is controllably orientatable relative to the first tissue-retaining member to reflect the received ultrasound energy back along different directions.

17. The ultrasound medical treatment system of claim 15, wherein the transducer and the reflector each focus ultrasound energy.

18. The ultrasound medical treatment system of claim 9, wherein the end effector has a longitudinal axis, and wherein one of the first and second tissue-retaining members at all times faces along a direction which is substantially parallel to the longitudinal axis.

19. The ultrasound medical treatment system of claim 18, wherein the one tissue-retaining member is the first tissue-retaining member.

20. A method for ultrasound medical treatment of a patient using the ultrasound medical treatment system of claim 18, comprising the steps of:
   a) endoscopically inserting the end effector into an ear, nose, or throat of the patient;
   b) guiding the end effector in the patient;
   c) identifying patient tissue for medical treatment at least in part from ultrasound imaging using the transducer;
   d) retaining identified patient tissue using the tissue-retaining device; and
   e) medically treating the retained patient tissue with ultrasound using the transducer and the reflector.

21. The ultrasound medical treatment system of claim 9, wherein the end effector has a longitudinal axis, and wherein one of the first and second tissue-retaining members at all times faces along a direction which is substantially perpendicular to the longitudinal axis.

22. The ultrasound medical treatment system of claim 21, wherein the one tissue-retaining member is the first tissue-retaining member.

23. A method for ultrasound medical treatment of a patient using the ultrasound medical treatment system of claim 21 comprising the steps of:
   a) inserting the end effector into the patient;
   b) retaining an intervertebral disk of the patient with the tissue-retaining device, wherein the intervertebral disk includes tissue; and
   c) medically treating the retained intervertebral disk with ultrasound to shrink the tissue using the transducer and the reflector.

24. A method for ultrasound medical treatment of a patient using the ultrasound medical treatment system of claim 21 comprising the steps of:
   a) inserting the end effector into the patient;
   b) retaining a joint of the patient with the tissue-retaining device, wherein the joint includes tissue; and
   c) medically treating the retained joint with ultrasound to shrink the tissue using the transducer and the reflector.

25. An ultrasound medical treatment system comprising an end effector insertable into a patient, wherein the end effector includes a tissue-retaining device, wherein the tissue-retaining device includes a first tissue-retaining member having an ultrasound imaging and medical-treatment transducer and includes a second tissue-retaining member having an ultrasound reflector, wherein the first and second tissue-retaining members are operatively connected together to retain patient tissue between the first and second tissue-restraining members and to release patient tissue so retained, and wherein the first and second tissue-retaining members always maintain a substantially parallel alignment, wherein the first tissue-retaining member is a distal end portion of a first tube, wherein a second tube is oriented substantially parallel to the first tube, wherein a first and second link members pivotally attached to the first tissue-retaining member and to the second tube at pivot points creating a hinged parallelogram defined by a proximal portion of the first tissue-retaining member, a distal portion of the second tube, and the first and second link members, wherein the reflector is disposed at a distal portion of the second tissue-retaining member and faces the transducer, and a cable operatively connected to the hinged parallelogram to move the second tissue-retaining member toward and away from the first tissue-retaining member.

26. The ultrasound medical treatment system of claim 25, also including an outer tube, and wherein the cable and the first and second tubes are disposed in the outer tube.

27. The ultrasound medical treatment system of claim 26, also including a handpiece, and wherein the cable and the first, second, and outer tubes are operatively connected to the handpiece.

* * * * *